United States Patent
Ellingboe et al.

(10) Patent No.: US 6,827,728 B2
(45) Date of Patent: Dec. 7, 2004

(54) PATIENT TEMPERATURE CONTROL SYSTEM

(75) Inventors: Bruce Ellingboe, Littleton, CO (US); Michael R. Hoglund, Mead, CO (US); Gary A. Carson, Golden, CO (US)

(73) Assignee: Medivance Incorporated, Louisville, CO (US)

( * ) Notice: Subject to any disclaimer, the term of this patent is extended or adjusted under 35 U.S.C. 154(b) by 0 days.

(21) Appl. No.: 10/215,116

(22) Filed: Aug. 8, 2002

(65) Prior Publication Data

US 2004/0030372 A1 Feb. 12, 2004

(51) Int. Cl.[7] .................................................. A61F 7/00
(52) U.S. Cl. ...................... 607/104; 607/108; 137/594
(58) Field of Search .................. 607/105, 108–112, 607/104; 137/597, 266, 584, 594; 5/713; 285/148.14

(56) References Cited

U.S. PATENT DOCUMENTS

| | | | |
|---|---|---|---|
| 3,894,213 A | 7/1975 | Agarwala | 219/297 |
| 4,118,946 A | 10/1978 | Tubin | 62/514 |
| 4,508,123 A | 4/1985 | Wyatt et al. | 128/692 |
| 4,691,762 A * | 9/1987 | Elkins et al. | 165/46 |
| 4,951,665 A | 8/1990 | Schneider | 128/400 |
| 4,982,736 A | 1/1991 | Schneider | 128/400 |
| 5,097,829 A | 3/1992 | Quisenberry | 128/400 |
| 5,323,808 A * | 6/1994 | Shimizu | 137/594 |
| 5,344,436 A | 9/1994 | Fontenot et al. | 607/104 |
| 5,411,541 A | 5/1995 | Bell et al. | 607/104 |
| 5,456,701 A | 10/1995 | Stout | 607/104 |
| D364,680 S | 11/1995 | Dye | D24/129 |
| 5,470,353 A | 11/1995 | Jensen | 607/104 |
| 5,507,792 A | 4/1996 | Mason et al. | 607/104 |
| 5,643,191 A | 7/1997 | Buckberg | 604/4 |
| 5,895,418 A | 4/1999 | Saringer | 607/104 |
| 5,944,362 A * | 8/1999 | Harle | 285/148.14 |
| 6,197,045 B1 | 3/2001 | Carson | 607/104 |
| 6,212,718 B1 * | 4/2001 | Stolpmann et al. | 5/713 |
| 6,238,427 B1 | 5/2001 | Matta | 607/104 |
| 6,394,138 B1 * | 5/2002 | Vu et al. | 137/884 |
| 6,425,414 B2 * | 7/2002 | Jorgensen et al. | 137/597 |
| 6,547,284 B2 * | 4/2003 | Rose et al. | 285/1 |

* cited by examiner

Primary Examiner—Roy D. Gibson
(74) Attorney, Agent, or Firm—Marsh Fischmann & Breyfogle LLP

(57) ABSTRACT

A system and method provide for the interconnection of a medical fluid processing system with at least one patient temperature control pad positionable on a patient. Includable in the system is at least one connector interconnected and/or interconnectable to the medical fluid processing system and at least one connector interconnected and/or interconnectable to the at least one temperature control pad, wherein the connectors include an orientation device which provides for interconnection of the connectors at a predetermined orientation.

86 Claims, 18 Drawing Sheets

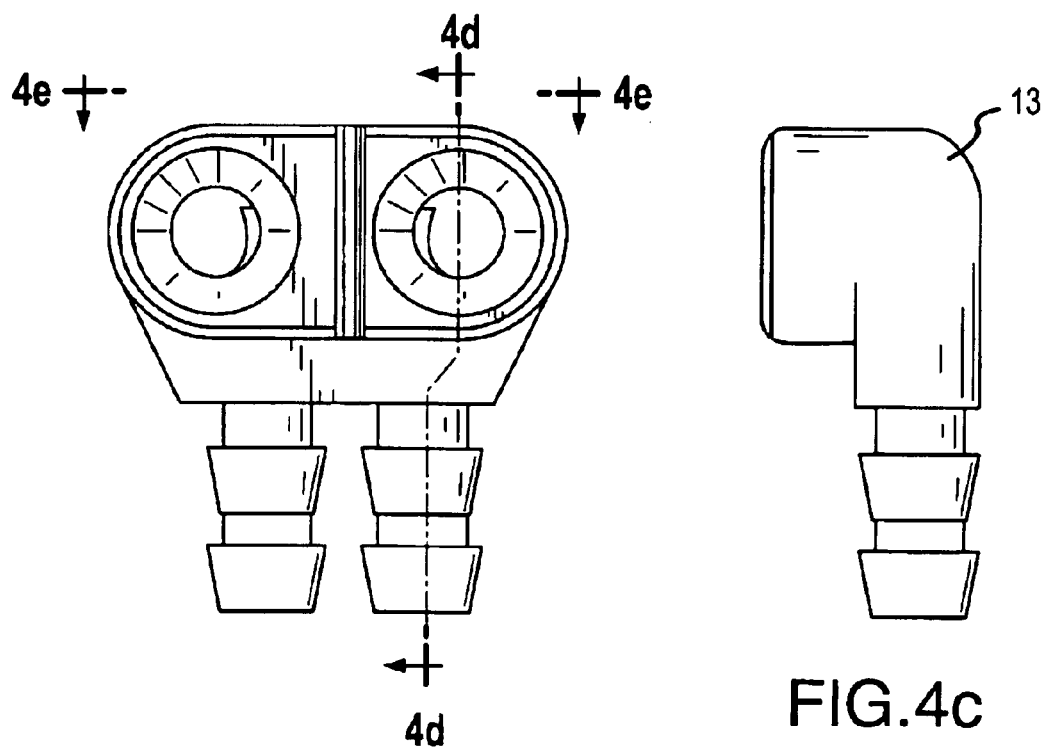
FIG.4b
FIG.4c
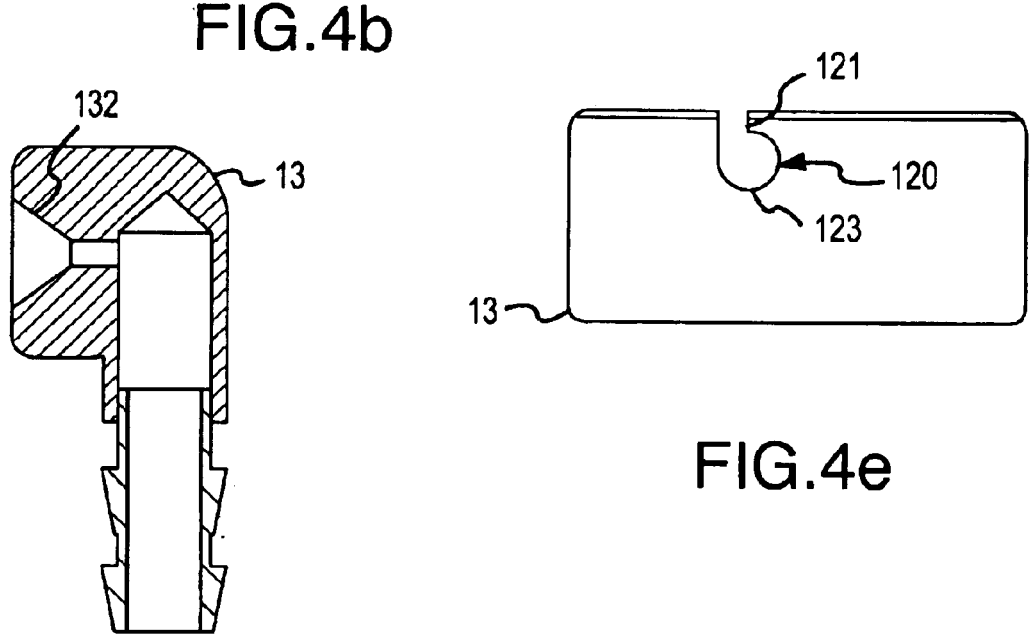
FIG.4d
FIG.4e

PATIENT TEMPERATURE CONTROL SYSTEM

FIELD OF THE INVENTION

The invention described herein relates to systems and methods for use in patient temperature control, and more specifically to devices employable for interconnecting a temperature control device such as a heating/cooling pad to a medical fluid processing apparatus.

BACKGROUND OF THE INVENTION

The use of contact pad system for selectively cooling and/or heating bodily tissue is known. In such systems a fluid, (e.g. water or air), is circulated through one or more pads to affect surface to surface thermal energy exchange with a patient. One highly effective contact pad and related system is disclosed in U.S. Pat. No. 6,197,045, hereby incorporated by reference in its entirety. As noted in U.S. Pat. No. 6,197,045, the ability to establish and maintain intimate pad to patient contact is often key importance to fully realizing medical efficacies with contact pad systems.

Temperature management or thermal regulation can be viewed in two different ways. The first aspect of temperature management includes treating at normal body temperature (i.e. cooling the body for elevated temperatures or warming the body for lower temperature). The second aspect of thermal regulation is an evolving treatment that employs techniques that physically control a patient's temperature to provide a physiological benefit, such as cooling a stroke patient to gain some degree of neuro protection.

In view of the foregoing, it may be appreciated that recognized medical applications for contact pad systems are ever increasing. By way of example, cooling pad systems may be utilized in early therapy to reduce neurological damage incurred by stroke and head trauma patients. Additional applications include selected patient heating/cooling during surgical procedure such as cardio pulmonary bypass operation.

As these and other medical applications have evolved, the present inventors have recognized the desirability of enhancing the flexibility and portability of thermal exchange fluid systems. More particularly, while heating/cooling contact pads systems have proven effective for many applications, the present inventors have recognized that additional performance and potential applications can be realized via implementation of further improved hose and connector device assemblies.

SUMMARY OF THE INVENTION

Disclosed herein is a system employable for providing patient temperature control which includes a medical fluid circulating system which includes at least one reservoir for circulating medical fluid. Included in the system is at least one first connector which is interconnected and/or interconnectable to a patient temperature control pad, wherein the first connector includes a body portion with a plurality of channels extending therethrough, as well as a connection end. Also included in this system is at least one second connector which is interconnected and/or interconnectable to the medical fluid circulating system wherein the second connector includes a body portion with a plurality of channels extending therethrough and a connection end configured to engage the connection end of the first connector so as to create a plurality of sealed fluid paths through the first and second connectors when engaged. The first and second connectors are further configured to include at least one orientation device such that the first end second connectors are connectable at only a predetermined orientation.

In one configuration of the invention, the first connector may be configured as a male connector end with an insertion end configured in the body portion. The second connector may be configured as a female connector further configured with a receiving end. The male and female connectors may be configured to include at least one orientation device employable to connect the male and female connectors at a desired relative orientation. The orientation devices employed in the male and female connectors may include an alignment flange positionable between openings in the insertion end of the male connector and an interference surface extending between the openings of the receiving end of the female connector such that upon attempting to interconnect the connectors at an orientation other than a predetermined orientation, the alignment flange and interference surface will come in contact, thus blocking insertion and interconnection.

In yet another configuration of the invention, the female connector may be configured with an engagement surface and the male connector may include an engagement device manipulable to engage and disengage the engagement surface of the female connector upon insertion in the receiving end. This engagement surface may be configured as a ledge structure incorporated into the body portion of the female connector.

The engagement device for the male connector may include at least one flex arm which extends substantially perpendicular from the body portion, as well as a latch arm connectable to the flex arm which is rotatable substantially about the connection point to the flex arm. Incorporated into the latch arm is an engagement portion configured to interlock with the engagement surface of the female connector. In yet another configuration of the invention, both the engagement portion of the first connector and the engagement surface of the second connector may be configured as interlocking lip structures.

The female connector assembly may be further configured to include at least one spring loaded valve device locatable within each of the channels which is configured to open upon insertion of the male connector in the channel and close upon its removal. An additional feature incorporated into the interlocking connectors is that once the insertion end of the male connector is within the female connector, the resistive force exerted by the valve spring on the insertion end of the male connector provides for maintaining contact between the engagement surface and engagement devices such that inadvertent disengagement of the connectors is substantially avoided.

In yet another configuration of the invention, the male connector includes a plurality of the engagement devices which require substantially simultaneous manipulation during the engagement and disengagement procedure. In particular, the male connector may be configured such that the insertion end of the male connector is not removable from the receiving end of the female connector until a further insertion force is exerted on the male connector further compressing the spring loaded valve device such that the interlocking lips are moved clear of each other. The plurality of engagement devices on the male connector are then simultaneously manipulated (such as with a thumb and finger) so as to clear the engagement surfaces. At this point, the insertion force is reversed and the male connector is removable.

In yet another configuration of the invention, the female connector may be further configured to include a rotatable engagement device in a receiving end and the male connector configured to include at least one engagement portion configured to receive the rotatable engagement device. Further, the male and female connectors may be configured such that at a first rotational orientation for the rotatable engagement device, the device will pass within the engagement portion of the male connector, and at a second rotational orientation the device will mechanically contact a portion of the male connector such that the male and female connectors are mechanically engaged.

The male connector may be further configured to be connectable and/or connected to a one piece hose section which includes a plurality of fluid channels formed therethrough. Still further, the one piece hose section may be connectable to at least one other connector. The other connector may be a female connector which includes one or more receiving ends for interconnecting with one or more male connectors which in turn are interconnected and/or interconnectable with a patient temperature control pad.

Further described herein is a system for circulating medical fluid through a temperature control pad wherein the system includes a female machine connector which is mountable on a medical fluid processing system. The female machine connector is further interconnected and/or interconnectable to a patient temperature control pad assembly which includes a male machine connector configured to connect with the female machine connector, a hose assembly, and the patient temperature control pad(s). Incorporated in the female machine connector is a receiving end which is configured to receive and fluidly seal with a male machine connector end insertable therein. The receiving end is further configured to include an engagement device, wherein the engagement device, while positionable within the receiving end, may pass within a portion of a male machine connector that is insertable in the receiving end. The engagement device is further configured to be manipulated such that the male and female machine connectors are mechanically engaged, and a plurality of sealed fluid paths are established.

As part of the system described herein the female machine connector may be further configured such that the engagement device includes a rotatable element which is configured to pass within the engagement portion of a male machine connector at a first rotational orientation and engage the male machine connector at a second rotational orientation. The rotatable engagement device may include shaft portion with a semi circular shape and the engagement portion of the male machine connector may be configured as a slot which opens into a cylindrical section. In operation, the engagement device, at a first profile relative to the male machine connector, may pass within the slot and into to the cylindrical portion, and then upon rotation to the second rotational orientation, have a profile which is too large for the slot portion thus contacting the internal surfaces of the cylindrical section and providing mechanical engagement between the male and female machine connectors. As an additional feature the position of engagement portion in the male machine connector may provide for interconnection of the male and female machine connectors only at a predetermined orientation.

As part of the temperature control pad assembly, the male machine connector may be further connected to a one piece hose section with a plurality of channels passing there through. The one piece hose section may be further connectable to an intermediate connector device which is also in fluid communication with the channels through the one piece hose section. The intermediate connector device may be further connectable to at least one other connector in the temperature control pad assembly. In one configuration of the invention, the intermediate connector device may be configured as a female intermediate connector connectable with one or more male intermediate connectors.

The male intermediate connectors, which are part of the temperature control pad assembly, may include a body portion with a plurality of fluid channels extending therethrough, and an insertion end specially configured for passing within a portion of the female intermediate connector. The female intermediate connector is also configured with a plurality of fluid channels formed therethrough, and further includes at least one receiving end configured to receive an insertion end for the male intermediate connector(s). Incorporated into the external surfaces of both the intermediate connectors described herein may be at least one orientation device or surface employable to align the male and female intermediate connectors for interconnection purposes.

The orientation devices or surfaces may be incorporated in the body portion of the intermediate connectors such that the insertion end for the male intermediate connector and/or the receiving end of the female intermediate connector include at least one non-symmetrical feature. This non-symmetrical feature may comprise an alignment flange extending between the fluid channels on the male intermediate connector, and/or a member incorporated in the receiving end of the female intermediate connector which extends between two openings incorporated therein. In the situation where the male intermediate connector is inserted within the receiving end at an incorrect orientation, the alignment flange will contact the orientation surface, thus blocking insertion therein.

Further with regards to the male and female intermediate connectors, these devices may be further configured to include various external engagement surfaces and devices which maintain engagement during operation of the system described herein. In one configuration of the invention, the female intermediate connector may be configured with at least one engagement surface and the male connector configured with at least one engagement device manipulable to engage and disengage with the engagement surface of female connector upon insertion in the receiving end. The engagement surface of the female intermediate connector may be configured as a ledge incorporated into body. The engagement device incorporated in the male intermediate connector may include at least one flex arm extending substantially perpendicular from the body portion of the male intermediate connector, a latch arm positionable at an end of the at least one flex arm. The flex arm may be further configured to include an engagement portion whereby the engagement portion is rotatable about the flex arm portion through manipulation of the flex arm at a point opposite the engagement surface relative to the flex arm.

In employing the engagement devices described above, the female intermediate connector may be further configured with at least one spring loaded valve device locatable within the fluid channels which opens and closes depending on the insertion status of a male intermediate connector end. The engagement surface of the female intermediate connector may be configured to include an interlocking lip portion which is configured to receive an interlocking lip configured into the latch arm of the male intermediate connector. These interlocking lips are specially configured such that upon insertion of the male intermediate connector within the insertion end of the female intermediate connector, the valve springs of the internal valve device are compressed and upon releasing the male intermediate connector the springs uncompress thus pushing the interlocking lips together. The relative surfaces of these lips are configured such that they resist any lateral movement of the connector device and connector surface with regards to the body portions of the male and female intermediate connectors.

In yet another configuration of the invention, the male intermediate connector may include a plurality of the engagement devices which require substantially simultaneous manipulation during the engagement and disengagement procedure. In particular, the male intermediate connector may be configured such that the insertion end of the male intermediate connector is not removable from the receiving end of the female intermediate connector until a further insertion force is exerted on the male intermediate connector further compressing the spring loaded valve device such that the interlocking lips are moved clear of each other. The plurality of engagement devices on the male intermediate connector are then simultaneously manipulated (such as with a thumb and finger) so as to clear the engagement surfaces. At this point, the insertion force is reversed and the male intermediate connector is removable.

BRIEF DESCRIPTION OF THE DRAWINGS

FIGS. 4a–e disclose views of the male machine connector.

DETAILED DESCRIPTION

Figure 1:
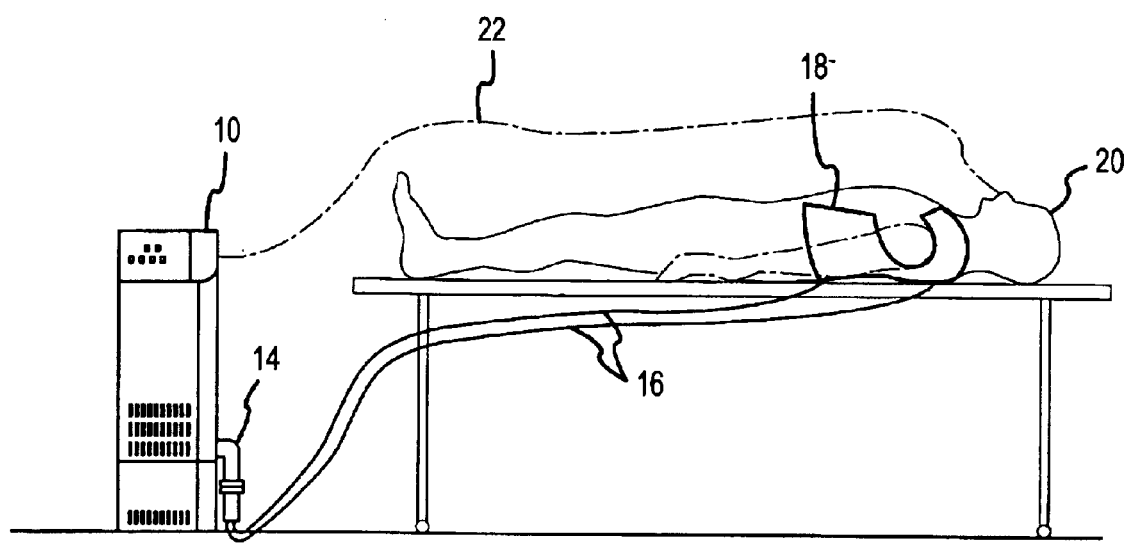
FIG. 1 is a view of a patient temperature control system with which the present invention may be employed.

Disclosed in FIG. 1 is an exemplary configuration of the temperature control system which is employable to provide heating/cooling of a patient 20. By way of example, pads 18 positionable on a patient 20 may be of the type described in U.S. Pat. No. 6,197,405. The system 10 is employable for circulating temperature control fluid through the pad 18. The system 10 may include a circulating pump for drawing fluid (e.g. water) through the pads, a circulating reservoir as well as one or more heat exchange devices for heating/cooling fluid circulating through the system. Also included may be a temperature sensor 22 employable for monitoring patient temperature.

Interconnecting the patient temperature control system 10 and the pads 18 is hose and connector assembly 14. Included in the assembly 14 may be one or more individual connectors, as well as lengths of hose 16 which act as delivery and return lines for the fluid circulated between system 10 and pads 18.

Figure 2:
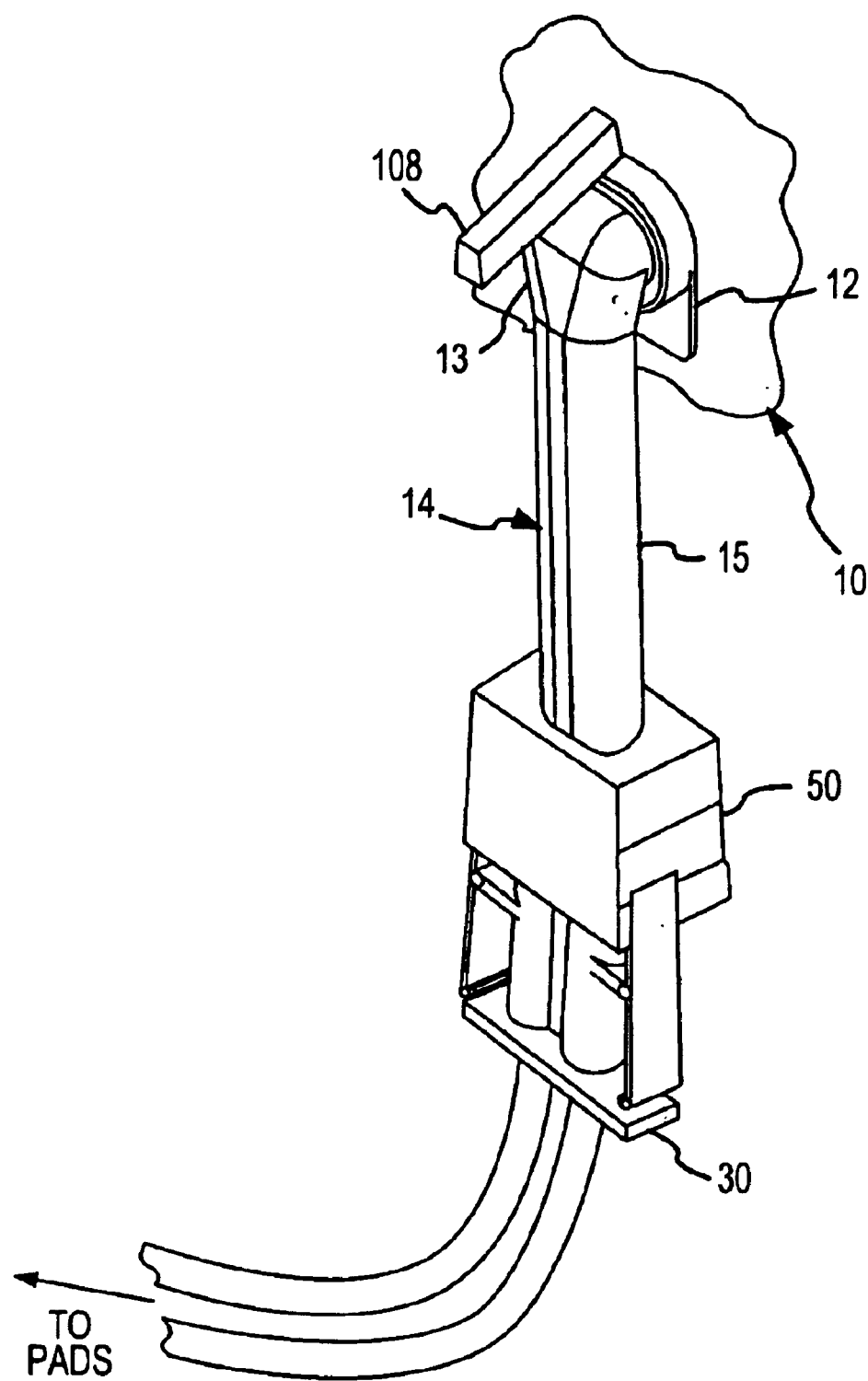
FIG. 2 is a view of one configuration of a hose and connector assembly.

Disclosed in FIG. 2 is a view of the hose and connector assembly 14 interconnected with system 10, specifically including the various connectors which may be employed in order to connect the patient temperature control system 10 to the patient temperature control pad(s). Shown in particular is female machine connector 12, which provides for the attachment of the hose assembly 14 to the control system 10. The female machine connector 12 may be incorporated into system 10 and be in fluid communication with the various reservoirs and heat exchange devices included therein. The female machine connector 12 may include at least one receiving end for receiving a male machine connector 13 portion of the hose and connector assembly 14. To facilitate the connection with the male machine connector 13, the female machine connector 12 may include a connection device 108 which is manipulable to establish a fluid tight connection. The details of female machine connector 12 will be discussed in greater detail below.

As noted, the hose assembly 14 includes a male machine connector 13 configured to be insertable within the female machine connector 12 and be engaged. The male machine connector 13 may be attached to one-piece hose apparatus 15 which is further in connection with female intermediate connector 50. As will be described in greater detail below, the female intermediate connector 50 may include one or more receiving ends configured to receive and engage any number of male intermediate connectors 30. The male intermediate connectors 30 are further connectable through hoses 16 to the patient temperature control pads. The connection to the patient temperature control pads may be through a single length of hose or through various lengths of hose interconnected using one or more male and female intermediate connector combinations.

Figure 3A:
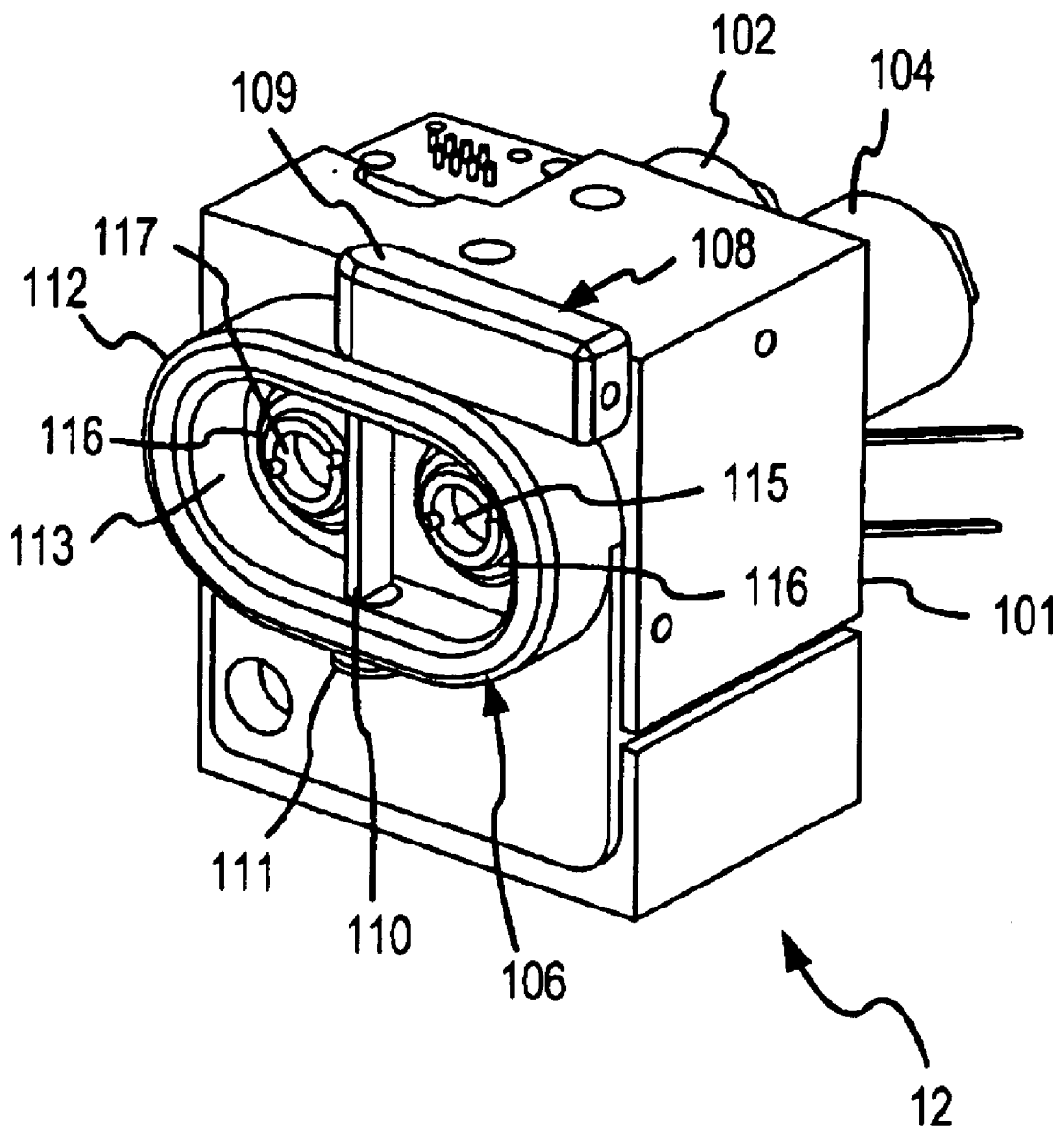
FIGS. 3a and b are views of the female machine connector.

With regards to the individual connectors, disclosed in FIGS. 3a and b are perspective and front views of female machine connector 12 which is mountable within the housing of temperature control system 10. Included in the female machine connector 12 is a receiving end 112 specially configured for receiving an insertion end 119 of a male machine connector 13. Included in particular is a wall structure 106 extending outward from the body 101 of connector 12. Within the wall structure is a cavity 113, which includes a cross section sized to fit with the insertion end 119 of a male machine connector 13 at a substantially close tolerance. Located within the receiving end 112 are openings for fluid channels 115 and 117 which extend above the floor of the cavity 113 and where each include at least one gasket device 116 for establishing a fluid tight seal. The fluid channels 115 and 117 pass through the female machine connector 12 and exit through channels 104 and 102 respectively. When installed in the temperature control system 10, these channels provide for the circulation of fluid to and from internal components of the system.

Extending within the cavity 113 is a rotational engagement device 108 which is configured to pass within an engagement portion of a male machine connector 13, and upon rotation mechanically engage said male machine connector 13. Included as part of the rotatable connection device is engagement shaft 110 which in the configuration of the invention shown in FIG. 3a is configured with a cross sectional shape of a semi-circle. The use of a semi-circle is exemplary, and any number other cross sectional shapes may be employable for this purpose.

Figure 3B:
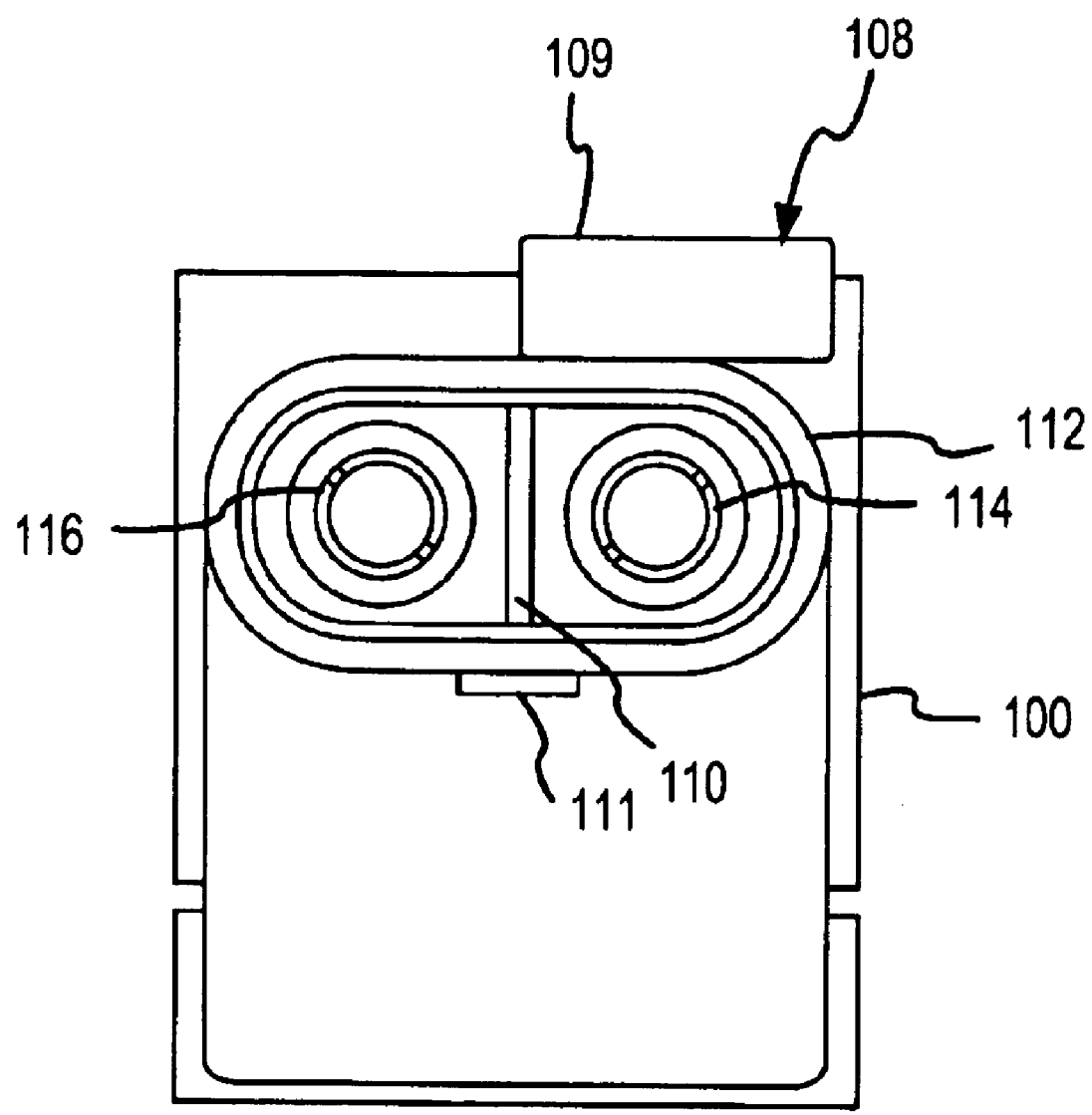

As can be better seen in the front view of FIG. 3b, the rotatable engagement device 108 further includes a retaining end 111 which passes through the wall portion of the cavity 113 and supports the engagement shaft at one end. At the opposite end of the engagement shaft 110 is the rotatable handle 108 which is rotatable to provide for the rotation of the engagement shaft 110. The handle portion 108 further includes retaining end portion which also passes within the wall structure 106. At either end of the shaft 110, the hole through the wall 106 provides a bearing surface for rotation of the shaft 110.

Figure 4A:
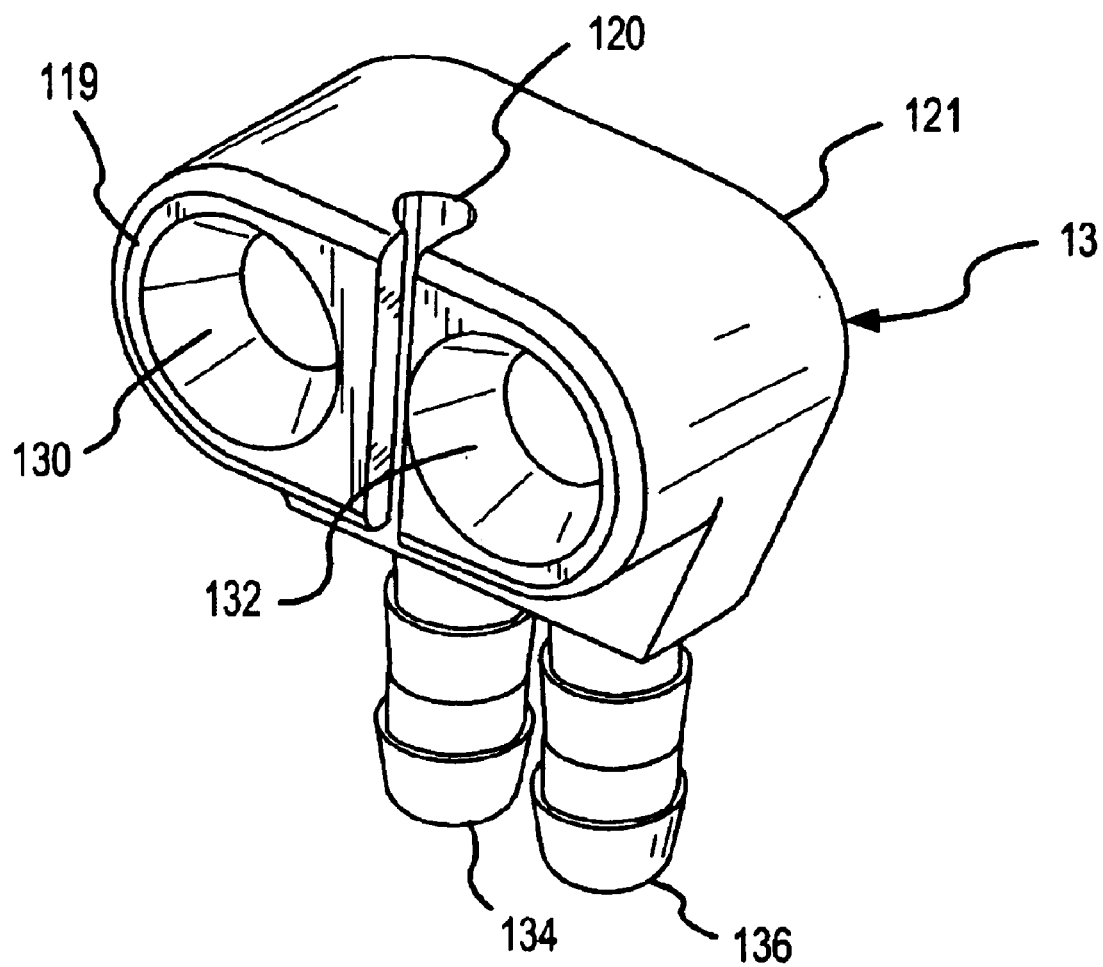

Disclosed in FIG. 4a is a geometric view of the male machine connector 13 employable to interconnect with female machine connector 12. The male machine connector 13 includes a body portion 121 through which two fluid channels 130 and 132 extend from insertion end 119 to attachment portions 134 and 136, respectively. The insertion end 119 disclosed herein is configured in an oval and/or racetrack type shape, although one skilled in the art would realize that any number of shapes is employable. Further, in the configuration shown in FIG. 4a, the fluid channels are configured to turn at substantially a 90° angle; however, one skilled in the art would realize that any number of configurations is possible.

As is seen in the cross section view of the connector in FIG. 4d, the interior surface fluid channels 130 and 132 are configured with a tapering cross section shape so that a fluid type seal may be created when the surfaces contact the fluid channels 115 and 117 in female machine connector 12. Attachment ends 134 and 136 may be configured to each attach to a hose for employable for circulating fluid to a remote device such as a temperature control pad. This configuration is especially applicable to connecting two lengths of hose between the system 10 and the patient temperature control pads without the use of any intermediate connectors. Alternatively, the attachment ends 134 and 136 may be replaced by a one-piece structure connectable to the body portion 121, where the one-piece structure includes a plurality of fluid channels passing therethrough. The one-piece structure may be further connectable to an intermediate connector. This configuration, including all its components, will be discussed in greater detail below.

Further incorporated in the male machine connector 13 is at least one engagement portion 120 specially configured to receive and mechanically engage with the engagement shaft 110 of the female machine connector 12. A view of the engagement portion 120 can be seen in the top view of the male machine connector 13 in FIG. 4e. In this configuration, it is seen that the engagement portion 120 includes a narrow, substantially rectangular slot 121 which opens up into a larger substantially circular area 123. This configuration allows the engagement shaft 110 to pass within the smaller slot 121 at a first rotational orientation and then once within the cylindrical area 123, rotate to a second rotational position whereby the relative width of the shaft 110 is greater than the slot 121. At this second orientation, shaft 110 contacts a portion of the interior surface of the circular area 123 such that the male and female machine connectors 13, 12 are mechanically engaged. The rectangular slot 121 may be further configured in the connector to act as an orientation device. In one configuration of the invention the slot is positioned closer to one channel through the connector than the other. This non-symmetry has the effect that the male and female machine connectors 13, 12 may only be connected one relative orientation thus ensuring that fluid through the system flows in the proper direction.

Figure 5A:
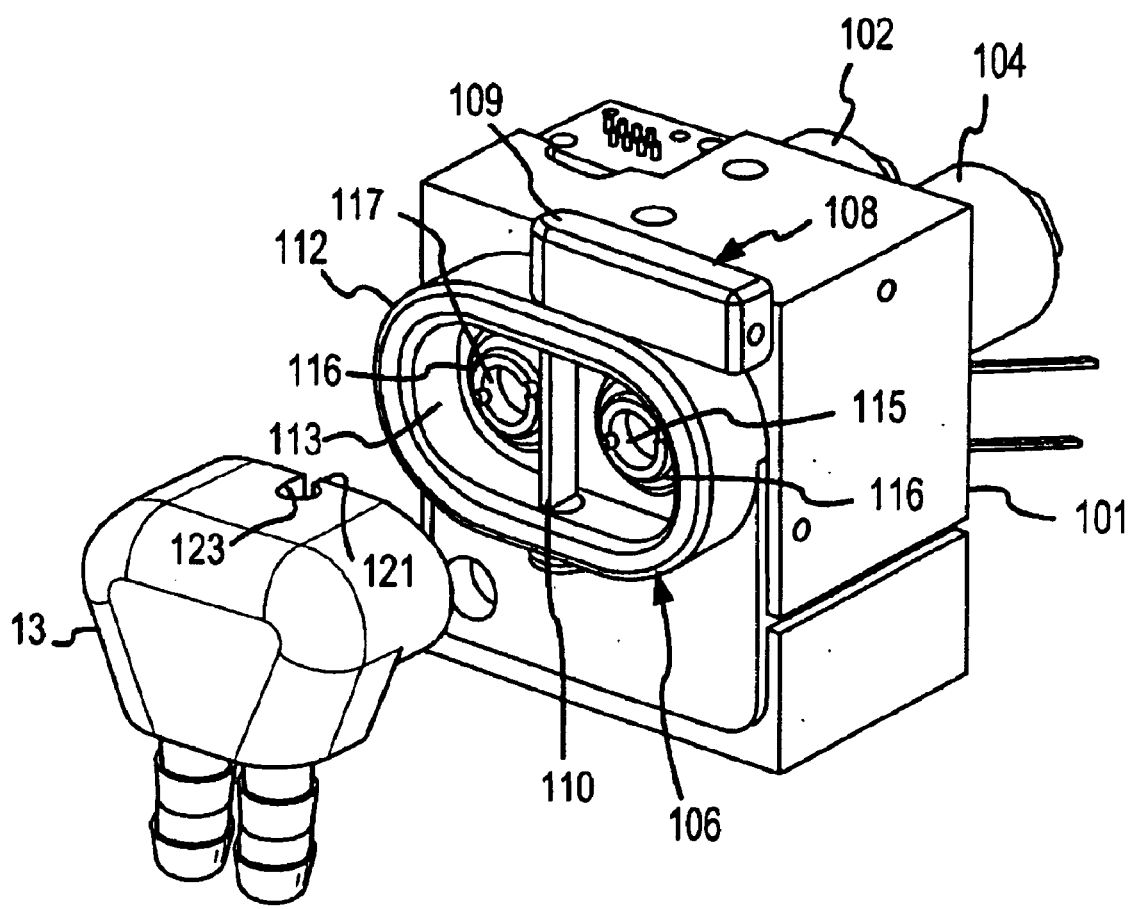
FIGS. 5a and b disclose geometric views of the male and female machine connectors in operation.
Figure 5B:
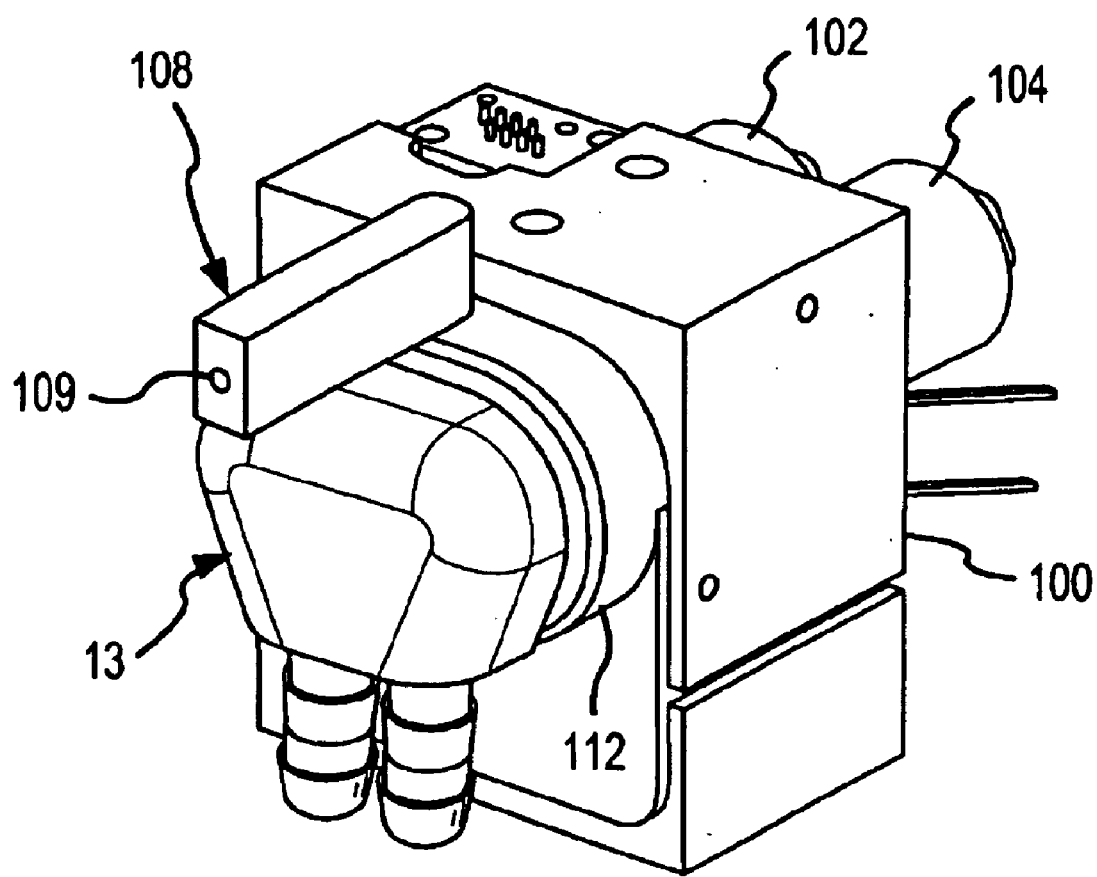

The views showing the engagement and disengagement of the male and female machine connectors 13, 12 are provided in FIGS. 5a and b. Seen in particular in FIG. 5a, prior to interconnection of these components, the male machine connector 13 is aligned with the receiving end 112 of the female machine connector 12. In particular, it is seen that the exterior of the male machine connector 13 is substantially the same shape as the receiving end 112 so that a substantially close tolerance fit may be achieved. Further, it is seen that the rotational connection device is in a first rotational position whereby the engagement shaft 110 is at its minimum cross section with regards to its position relative to engagement slot 121.

Once the components are aligned, the male machine connector 13 may be inserted in receiving end 112 in a manner such that the engagement shaft 110 passes within the slot 121. Once the internal channels of the male machine connector 13 head contact the protruding openings of the female machine connector 12 and the rotation shaft 110 passes within the cylindrical area 123, the handle of the rotational engagement device 108 may be rotated in a manner which is shown in FIG. 4b. This movement of the handle acts to rotate the engagement shaft 110 within the cylindrical portion 123 of the engagement slot 121 such that mechanical contact is created between the engagement shaft 123 and the interior surfaces of the cylindrical portion and a compressive force is applied between the male and female machine connectors 13, 12 such that a plurality of fluidly scaled channels through both connectors is created.

Returning again to FIG. 2, as part of a patient temperature control system, the male machine connector 13 may be further connectable to a hose assembly 14 employable for circulating medical fluid to and from the temperature patient temperature control pad. Included as part of the hose assembly 14 may be one or more intermediate connector devices which are employed to connect with hoses in fluid communication with the patient temperature control pad. The one or more intermediate connector devices may comprise at least one male intermediate connector 30 and at least one female intermediate connector 19 specially configured to engage with one another and further provide a plurality of sealed flow paths between the temperature control system and the temperature control pad for circulation of the medical fluid.

Figure 6A:
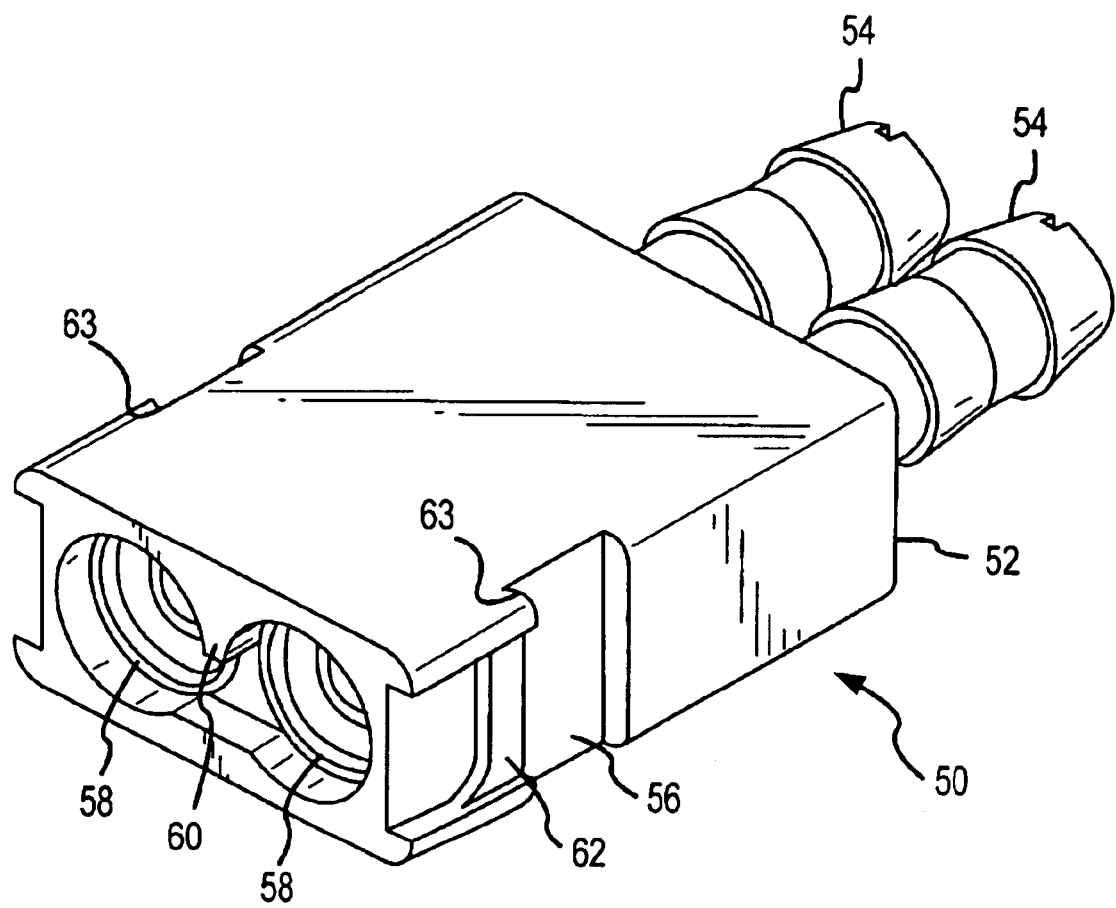
FIGS. 6a–c disclose views of one configuration of the female intermediate connector.

A geometric view of one configuration of a- female intermediate connector 50 is disclosed in FIG. 6a. Incorporated in the female intermediate connector 50 are hose ends 54 which are configured to compressibility fit within the attachment portion of a plurality hoses which may be further connectable, for example, to male machine connector 13. In an alternate configuration, which is shown in FIG. 2 and is to be described in greater detail below, the connection ends may be replaced the one-piece hose structure 15 with a plurality of flow channels formed therein. The one-piece hose structure 15 is further connectable to the male machine connector 13.

Figure 6B:
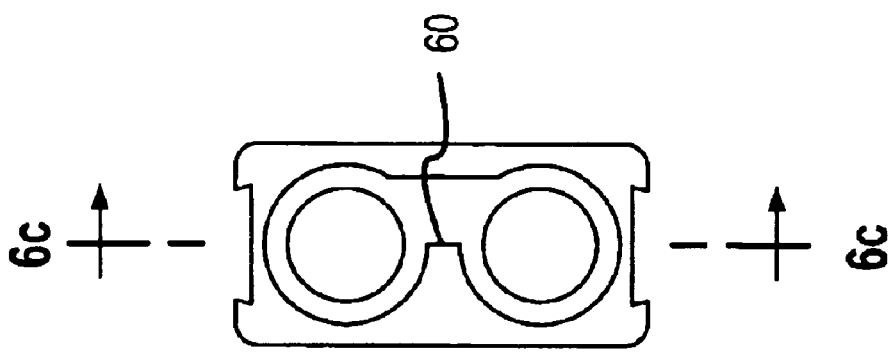
Figure 6C:
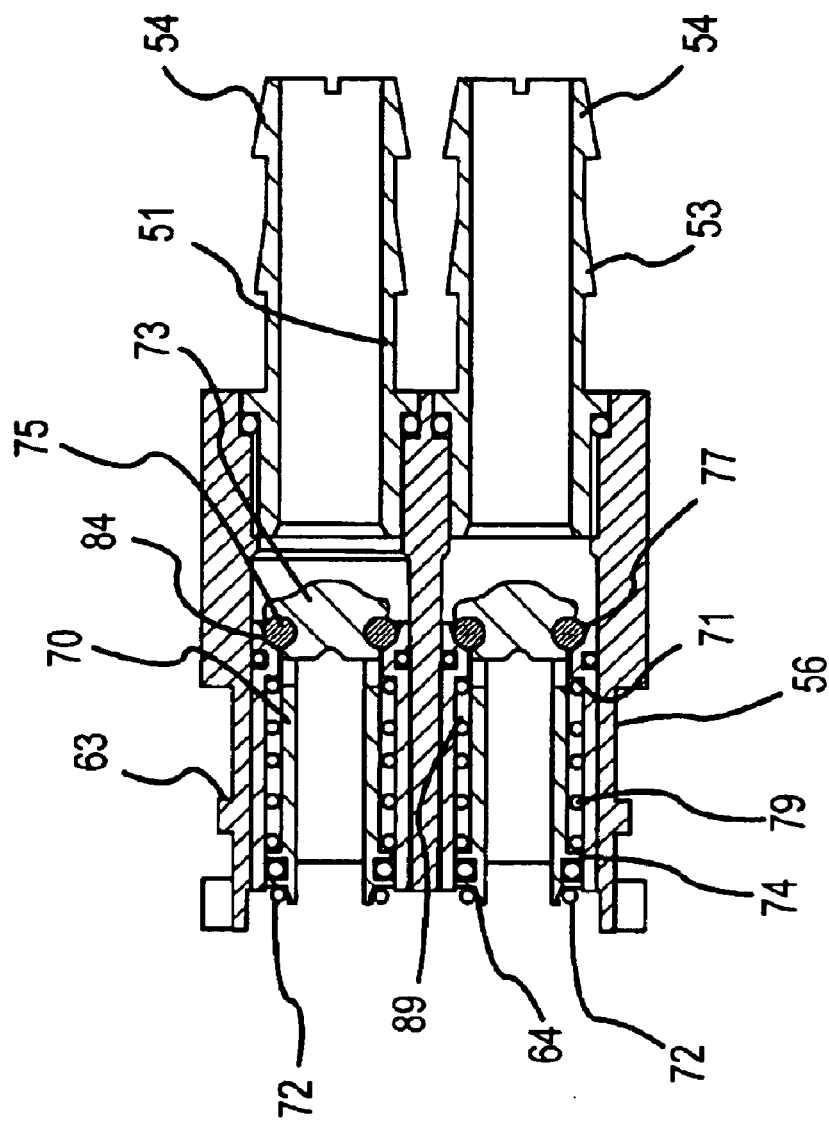

As seen in the cross sectional view of FIG. 6c, the female intermediate connector 50 further includes fluid channels 51 and 53 which extend from the hose ends 54 through body portion 52. The channels exit through receiving end 58. See FIG. 6a. Receiving end 58 is configured as a cavity in the body portion which is shaped to receive a portion of a male intermediate connector 30. Although the female intermediate connector 50 disclosed in FIGS. 6a–c is shown to include a single receiving end, other configurations of the female intermediate connector 50 may include a plurality of receiving ends, wherein one female intermediate connector 50 is connectable to a plurality of male intermediate connectors 30 simultaneously.

Continuing on with the female intermediate connector assembly 50, further included within the body portion 52 of the female intermediate connector is a moveable valve device which is manipulable to open and close upon insertion of the male connector. Returning again to the cross sectional view of FIG. 6c, the details of the valve device may be better viewed. A moveable valve device is positionable in each of the channels 51 and 53 for controlling the flow of medical fluid therethrough. Shown in particular, is a valve plunger 70 which has incorporated therein a number of openings 84, which depending on the position of the plunger in the channel, provide for fluid flow through the female intermediate connector 30. Surrounding the body portion of the valve plunger are springs 79, which are compressible against spring stop 71 when the male intermediate connector 30 is inserted. The insertion end 32 of the male intermediate connector 30 initiates movement of the plunger within the channels, such that the openings in the plunger are moved to a position which provides for circulation of the medical fluid.

Each plunger further includes an O-ring seal 72 which contacts an internal surface of the insertion end 32 of the male intermediate connector 30 when inserted. The plunger seal 74 is further employable to move with the plunger device and provide a fluid seal even while the plunger is moving or is moved. At the opposite end of the plunger device is a cap 73 which includes a valve seal 75 that provides for the sealing of the valve device upon removal of the male intermediate connector 30. The sealing occurs when the valve spring decompresses and moves the plunger back towards the receiving end. At this point, the valve seal 75 contacts seat 84 and seals off any fluid flow therethrough.

Returning again to FIG. 6a, further incorporated into the body portion 52 are a number of engagement surfaces 63 configured for receiving and engaging an engagement arm portion of the male intermediate connector 30. As was will be described in greater detail below, the engagement surface 63 is configured as a lip which interlocks with a corresponding lip configured on an engagement arm of an insertable male connector.

Disclosed in the view provided in FIG. 6b, is a view of orientation device 60 incorporated into the body portion 52. This orientation device provides a non-symmetrical feature to the receiving end 58 of the female intermediate connector 50, which in turn provides for the insertion of the male intermediate connector 30 at only a particular orientation. The desirability of this feature will be described in greater detail below.

Figure 7A:
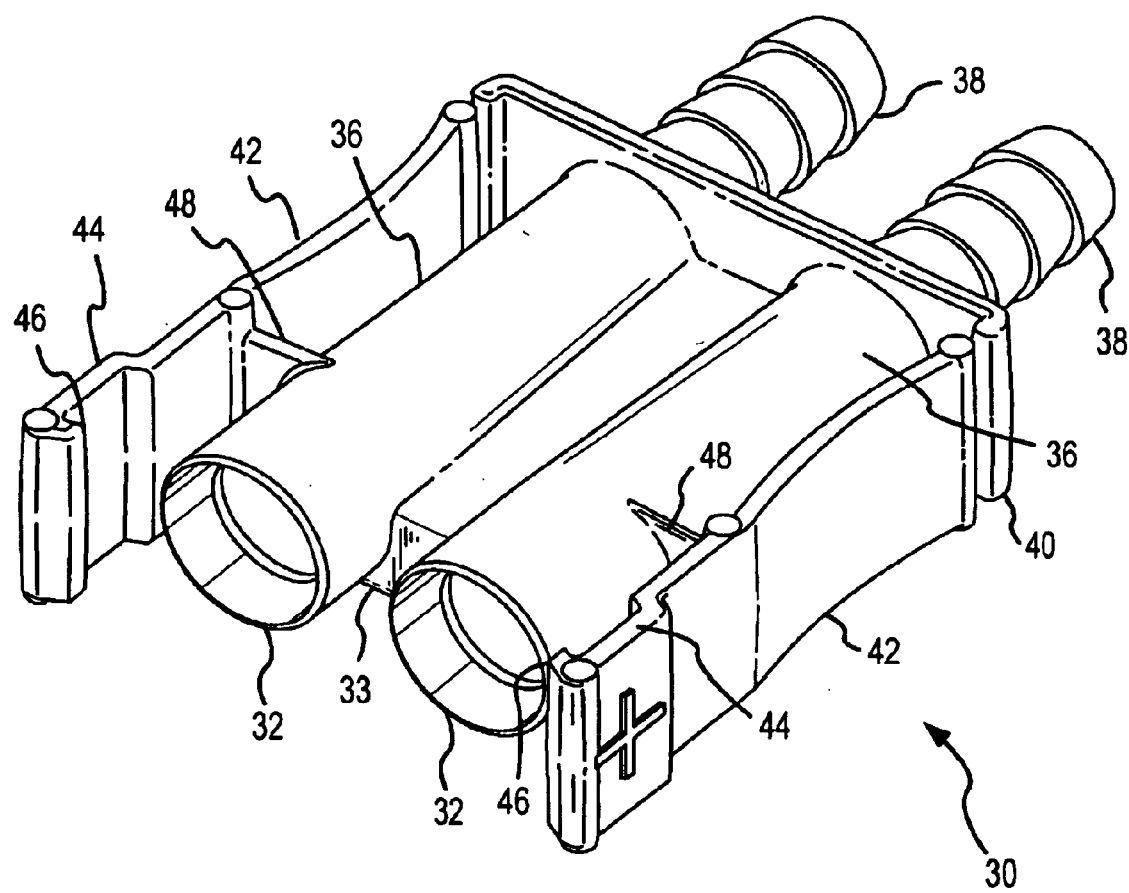
FIGS. 7a–c disclose views of the male intermediate connector.
Figure 7B:
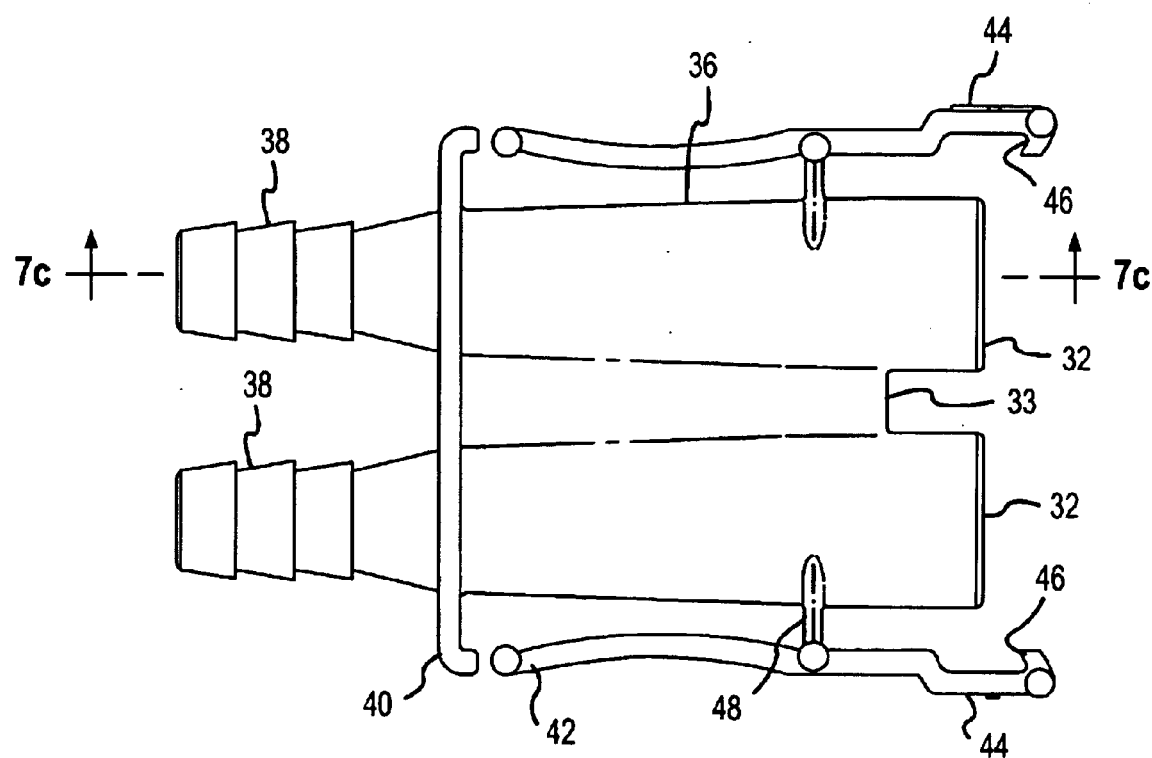
Figure 7C:
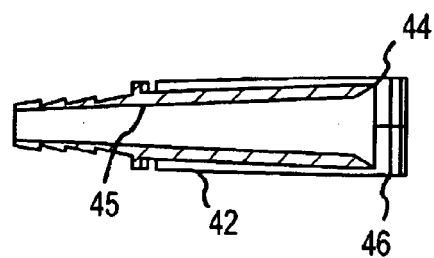

Views of one configuration of the male intermediate connector 30 configured to be interconnectable with the female intermediate connector 50 described above are provided in FIGS. 7a–c. Disclosed in FIG. 7a is a geometric view of the male intermediate connector 30. The male intermediate connector 30 includes a body portion 36 within which are formed fluid channels which pass from an insertion end 32 to a hose end 38. The hose end 38 is configured such that it is insertable within one end of a hose portion which in turn is interconnected and/or interconnectable to a patient temperature control pad or another connector. A removal/insertion arm 40 is configured to be employed in the insertion and removal of the male intermediate connector 30 with an female intermediate connector 50.

The insertion end 32 is configured to be insertable in a female intermediate connector 50. In particular, insertion end 32 may be configured to contact one or more sealing devices within a portion of the female intermediate connector 50 upon insertion so as to establish a fluid seal. During operation, depending on the direction of the flow, fluid will pass from insertion end 32 unobstructed to hose end 38 and vice versa. A cross sectional view of one of the fluid channels 45 through the male intermediate connector 50 is shown in detail in the view of FIG. 7c.

Also incorporated into the male intermediate connector 30 are one or more devices which provide for the engagement and proper alignment of the male intermediate connector 30 within a female intermediate connector 50. For engagement with the female intermediate connector 50, extending from the body portion 36 are one or more flex arms 48. The flex arms 48 may be constructed of a material which is the same or similar to the material use to form the body 36, wherein the flex arms 48 have sufficient flexibility to deform about the point of the attachment of the flex arm 48 to body 36. Further, attached to the flex arm 48 is latch arm 42 which is rotatable about an attachment point to flex arm 48 when a force is applied. When the force is removed, the elasticity of flex arm 48 returns the latch arm 42 to its original position.

Opposite the latch arm 42 portion is the attachment arm 44. Incorporated into the attachment arm 44 is an engagement lip 46 which is configured to interlock with a corresponding lip on an engagement surface 63 of a female intermediate connector 50. The attachment arm 44 and interlocking lip 46 of the male intermediate connector 30 are configured such that when a force is applied to the latch arm 42, which moves it closer to the body portion 36, the engagement arm 44 rotates away from the first end 32. When the force is released the elastic characteristics of the flex arm 48 returns the attachment arm with engagement lip 46 to its original position so that the engagement lip 46 may contact a corresponding engagement surface 63 on the female intermediate connector 50.

With regards to the alignment of the male and female intermediate connectors 50, further incorporated into the male intermediate connector 30 is orientation flange 33. Orientation flange 33 extends between the channels incorporated into body 36 and provides the functionality such that the male intermediate connector 30 may only be insertable in a female intermediate connector 50 at a particular orientation. In essence, this orientation device provides a non-symmetric feature to the insertable portion of male intermediate connector 30.

Figure 8B:
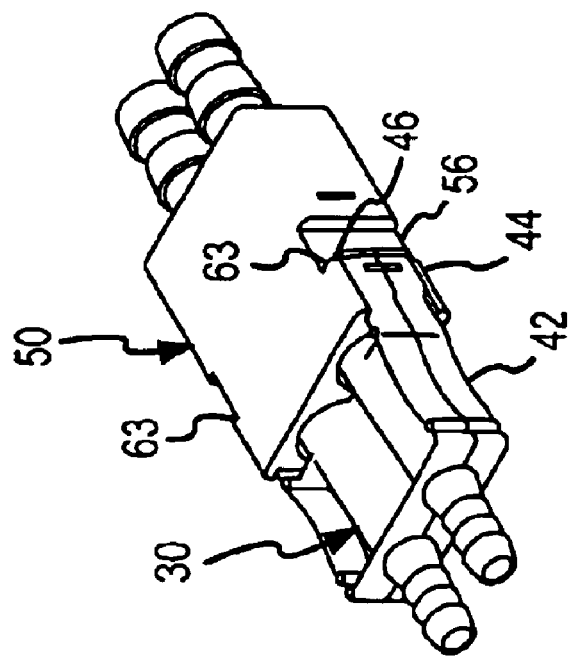
FIGS. 8a–f disclose views of the male and female intermediate connectors in operation.
Figure 8A:
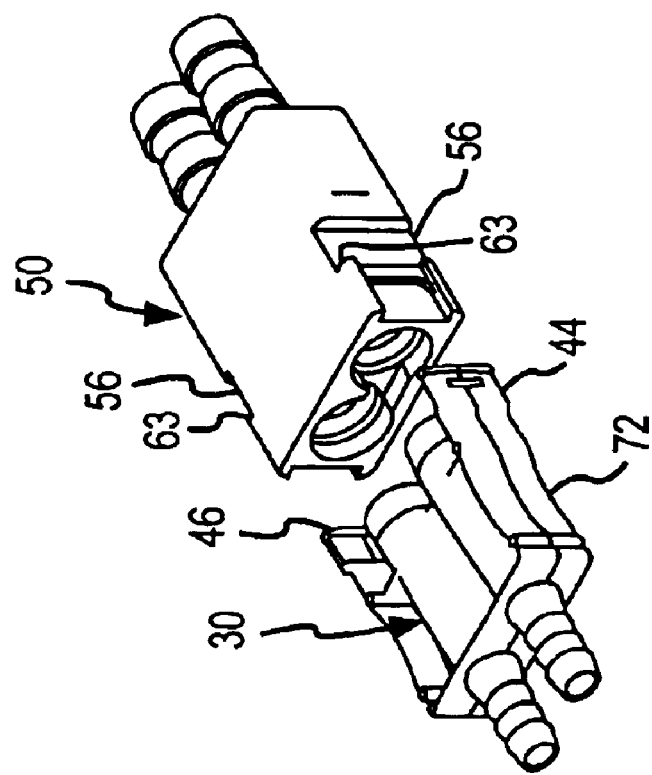
Figure 8C:
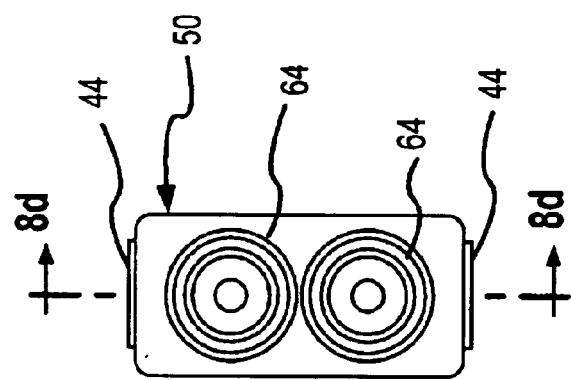

The engagement and disengagement of the male and female intermediate connectors may be better understood through study of FIGS. 8a–d. In particular, FIG. 8b shows the engagement of the male and female intermediate connectors, assemblies while FIG. 8a shows the connectors 30, 50 in a disengaged state. In order to initially engage the intermediate connectors the male and female intermediate connectors 30, 50 are first aligned. As part of the alignment process, the orientation flange 33 on the male intermediate connector 30 is positioned in a manner to as not to contact orientation device 60 upon insertion. More specifically, if the orientation device 60 contacts orientation flange 33 on the male intermediate connector 30, the male intermediate connector 30 is not insertable into the receiving end 58. Conversely, if the orientation device 60 is opposite the orientation flange 33 the male intermediate connector 30 is insertable in the receiving end 58 of the female intermediate connector 50 and a fluid tight connection may be made. The orientation devices provide the advantage that the wrong channels through the male and female intermediate connectors 30, 50 will not be fluidly connected, potentially affecting circulation of the medical fluid through the system.

Prior to insertion of the male intermediate connector 30 in the female intermediate connector 50, a force may be applied to attachment arms 42, preferably with one hand using, for example, the thumb and forefinger, which moves the attachment arms 42 towards the body portion 36 and the engagement arms 44 with interlocking lip 46 far enough away so as to clear the exterior body of the female intermediate connector 50.

The insertion end 32 of the male intermediate connector 30 may then be inserted within the receiving end 58 of the female intermediate connector 50 such that the interior surface of the insertion end 32 contacts the O-ring seal 72 on the valve plunger 70 which in turn pushes the plunger and compresses the valve spring. The plunger is moved to the point that the openings in the plunger body allow for fluid flow through the female intermediate connector 50.

Figure 8D:
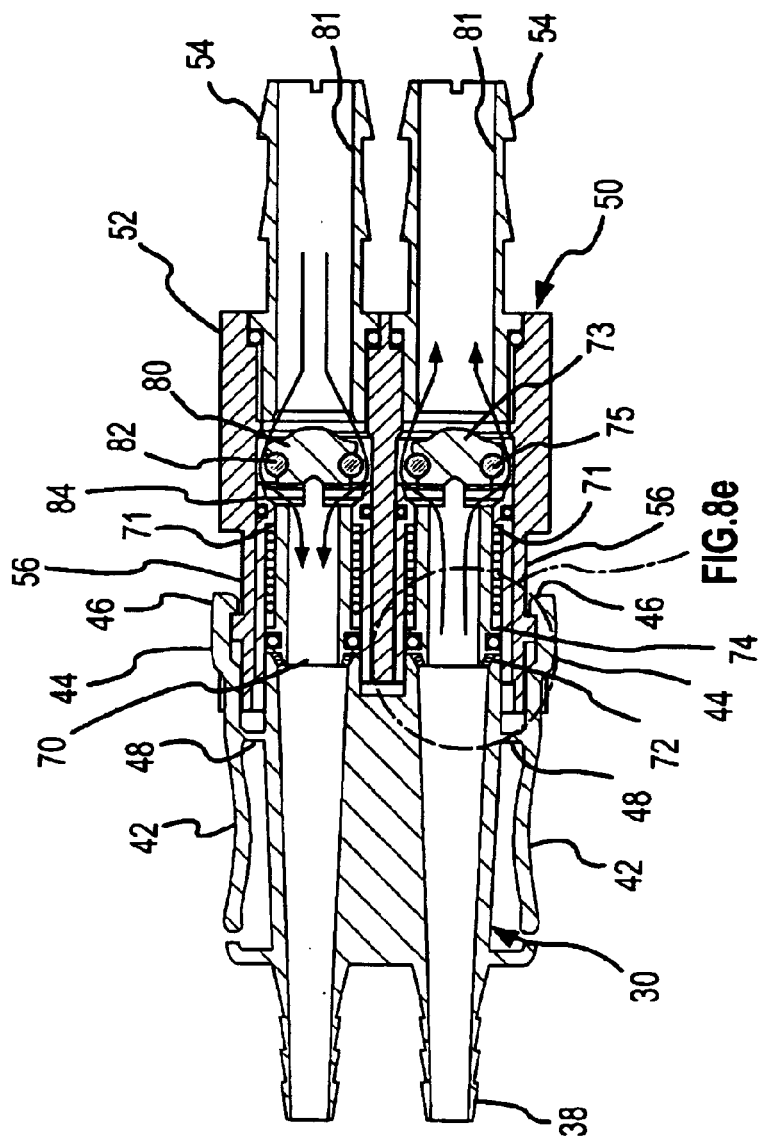

An example of an open valve within the female intermediate connector 50 is shown in the cross sectional view provided in FIG. 8d. As can be seen, when the male intermediate connector 30 is inserted, the valve spring 79 is compressed and head 80, with seal 82, is moved clear of valve seat 84 thus providing a fluid through the connector. As can be seen, in a circulating system such as the one described herein, the fluid may flow in different directions in the different channels.

Figure 8F:
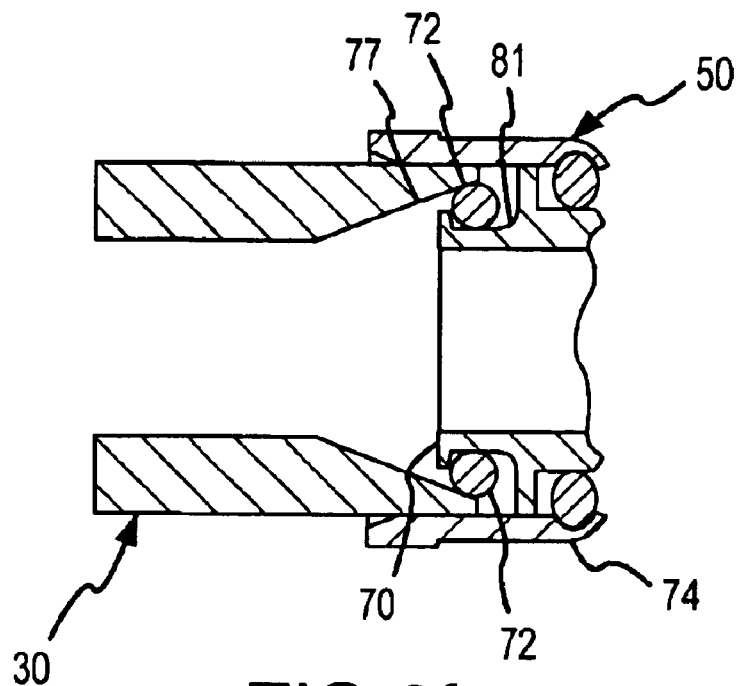
Figure 8E:
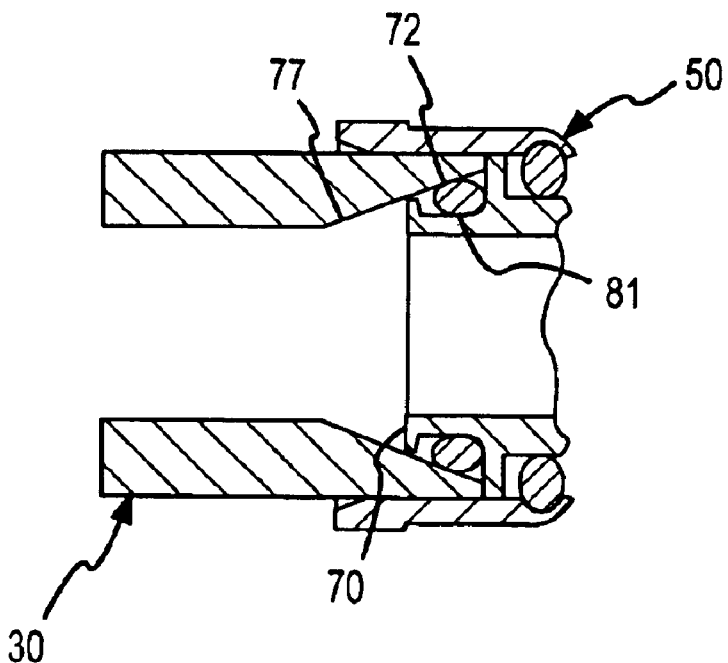

The fluid tight seal created between the male and female intermediate connectors 30, 50 upon connection may be better understood through the sectional views provided in FIGS. 8e and f. Disclosed in the view of FIG. 8e is a cross sectional view of the male intermediate connector 30 and female intermediate connector 50 in contact just prior to establishing the fluid tight seal. As can be seen, the male intermediate connector 30 includes an internal, tapered surface 77 which contacts an O ring 72 mounted on the valve plunger 70. The valve plunger 70 has an external tapered surface 81 that contacts the opposite side of the O-ring.

As the male intermediate connector 30 is pushed into the female intermediate connector 50, the O-ring 72 rolls between the two tapered surfaces 77 and 81. During the insertion, the O-ring rolls rather than slides against the mating surfaces so that wear of the O-ring is minimized. Further, rolling rather than sliding also reduces the force required to engage the two connectors. Since the two surfaces in contact with the O-ring are tapered, the O-ring is compressed as the male intermediate connector 30 is moved along the axis of the flow channel for the female intermediate connector 50.

Shown in FIG. 8f is a view of the male and female intermediate connectors 30, 50 fully engaged. As is seen, because the internal tapered surface 77 of the male intermediate connector has a larger taper angle than the external surface of the valve plunger, thus the O-ring is squeezed into a wedge shape. The O-ring gland area is tapered so that an increased vacuum inside the connectors pulls the O-ring into a smaller section of the gland. This increases the compression in the O-ring, which in turn increases the contact stress between the O-ring and tapered surfaces. The result is that increased vacuum improves the seal by tightening the O-ring in the gland.

The fluid tight seal described above is maintained by the mechanic engagement of the male and female intermediate connectors 30, 50. The mechanical engagement of the male and female intermediate connectors 30, 50 may be better understood through further study of FIG. 8d. Once the engagement portion 46 of attachment arm 44 passes within the engagement area 56 on the exterior of the female intermediate connector 50, the latch arm of the male intermediate connector 30 may be released, which in turn rotates the engagement lip 46 such that it contacts engagement area 56. Releasing the male intermediate connector 30 has the further effect that the compressed valve springs begin to uncompress, thus moving the engagement lip 46 into engagement surface 63, thus interlocking the two surfaces. The compressive force applied by the valve springs keeps the two surfaces in contact, and the diagonal direction, relatively, of the surfaces resists lateral movement of the engagement arm with respect to the female connector body thus maintaining engagement between the male and female connectors.

In order to disengage the male intermediate connector 30 from the female intermediate connector 50, an insertion force is applied to the male intermediate connector 30, further moving the valve plunger 70 and further compressing the valve spring. The further movement of the male intermediate connector 30 acts to move the engagement devices and engagement surfaces clear of each other. Forces are then applied simultaneously (using the thumb and forefinger, for example) to all of the latch arms 42 to move them towards the body 36 of the male intermediate connector 30. The application of these forces acts to move the engagement arms 44 away from the body portion 52 of the female intermediate connector 50, whereby maintaining the force on the latch arms 42 the insertion force may be reversed and the male intermediate connector 30 removed. It should be noted that in the configuration of the invention described herein, simultaneous application of force to all latch arms 42 is necessary to perform the removal of the male intermediate connector 30. If one the engagement arms is not moved, the interlocking lip 46 on the arm is not moved and will contact the corresponding interlocking lip 46 on the engagement surface, thus interfering with removal of the male intermediate connector 30. The necessity of this simultaneous movement is a safety feature which acts to avoid inadvertent disconnections of the male and female intermediate connectors 30, 50.

As was discussed above, the male machine connector 13 may be included as part of a connector assembly. This connector assembly may include a male machine connector 13, an intermediate one-piece hose 15, as well as a female intermediate connector 50. In one configuration of the invention the connector assembly may be a unitary piece, in that it may be made up of a number of different pieces, and manufactured in manner such that it cannot be disassembled without damaging its function. Disclosed in FIGS. 9a–f are various views of this connector assembly.

Figure 9A:
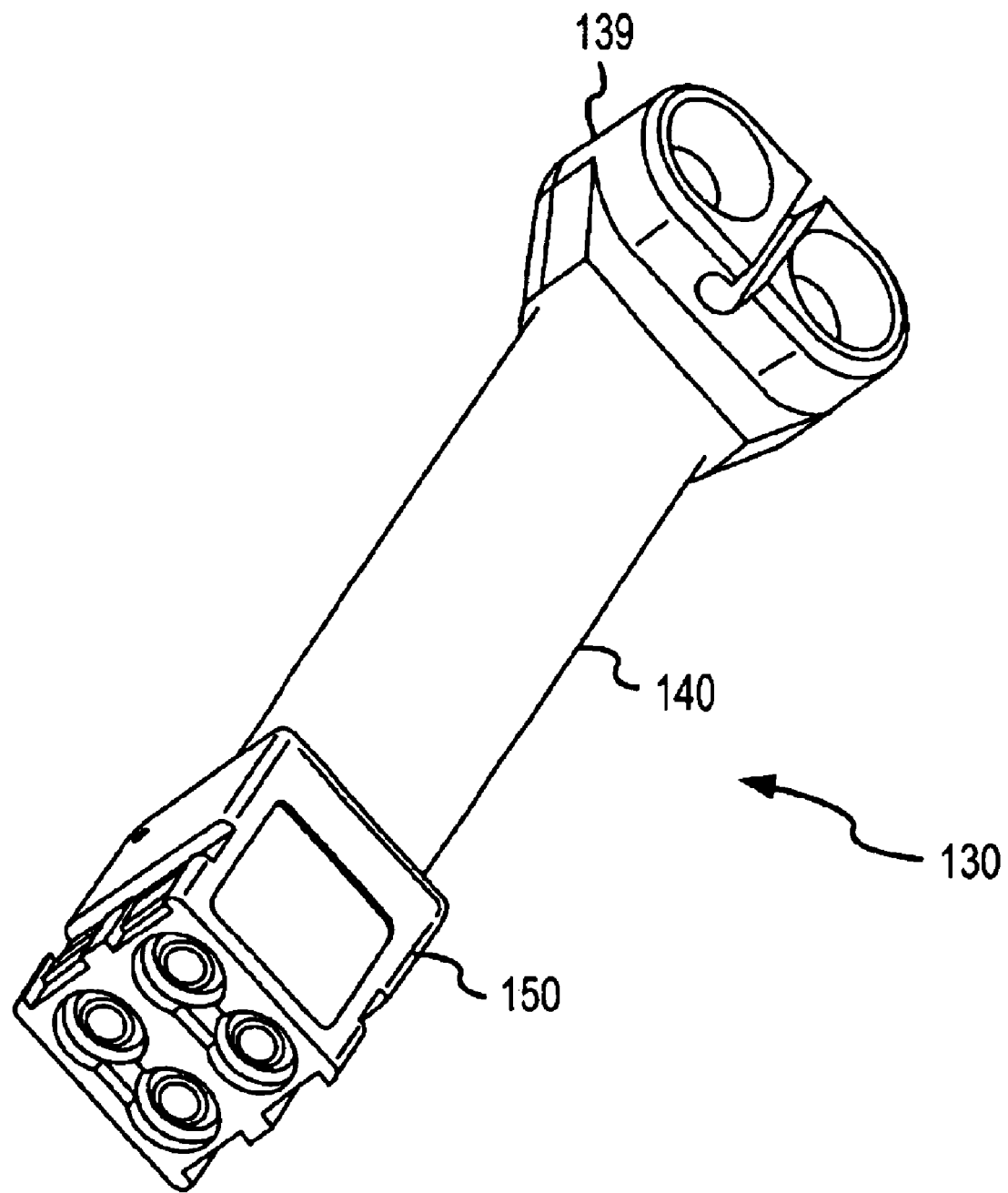
FIGS. 9a–f disclose views of one configuration of the male connector assembly.
Figure 9F:
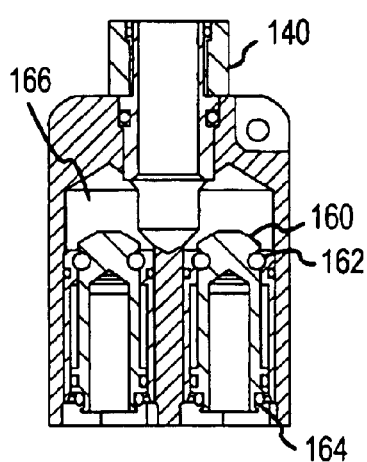
Figure 9E:
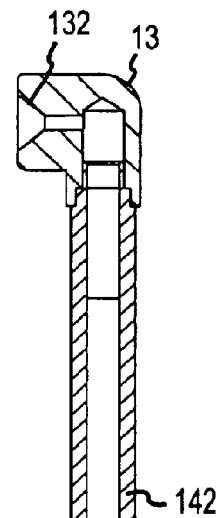
Figure 9B:
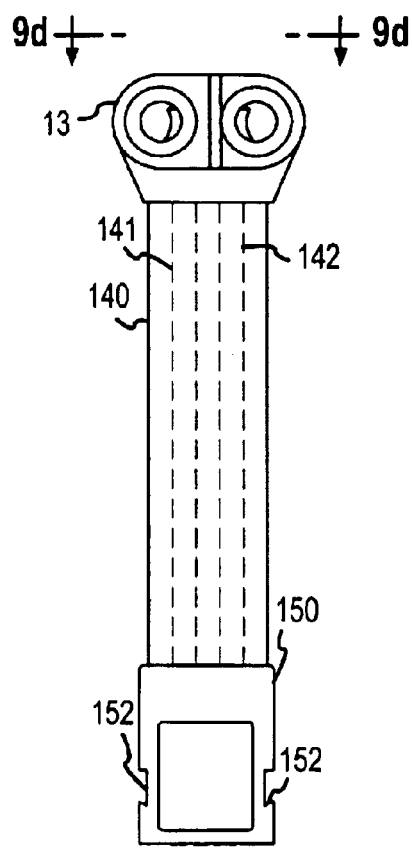
Figure 9C:
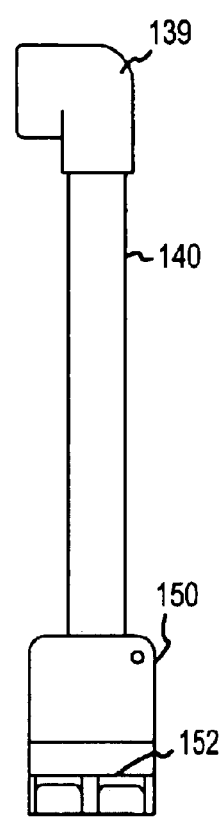

Disclosed in FIG. 9a is a geometric view of the connector including a male machine connector 13 connected to the one-piece hose section 140, which in turn is connected to female intermediate connector assembly 150. As seen in FIG. 9b and the cross sectional view of FIG. 9e, incorporated into the hose section 140 are fluid channels 140 and 142. The channels are in communications with channels through the male machine connector 13 and the female intermediate connector 50 assembly portions. Hose section 140 may be formed out of any number of hard plastic, rubber, or composite materials of sufficient stiffness.

Figure 9D:
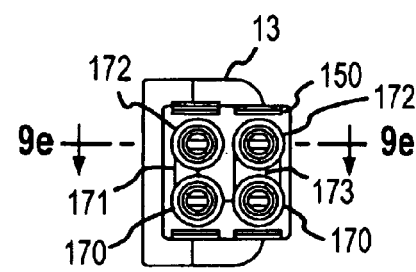

In the configuration shown in FIG. 9a, the female machine connector assembly is configured to interconnect with a maximum of two male intermediate connector assemblies. As seen in FIG. 9d, configured into the bottom of female connector assembly 150 are two receiving ends 171 and 173, where each end includes openings 170 and 172 to the fluid channels incorporated therein. As seen in the cross sectional view, each of the channels includes a valve assembly which operates in the same manner as described above for the female intermediate connector 50. For the channels which circulate fluid in the same direction, such as those shown in the cross sectional view of FIG. 9e, they are further in communication with a common manifold 166 which is further in communications with a channel, channel 142 in this view, of the hose section 140. It is further seen that each receiving end 171 and 173 includes a set of engagement surfaces 152 configured for engaging and interlocking with the engagement devices incorporated in the male connectors.

Figure 10:
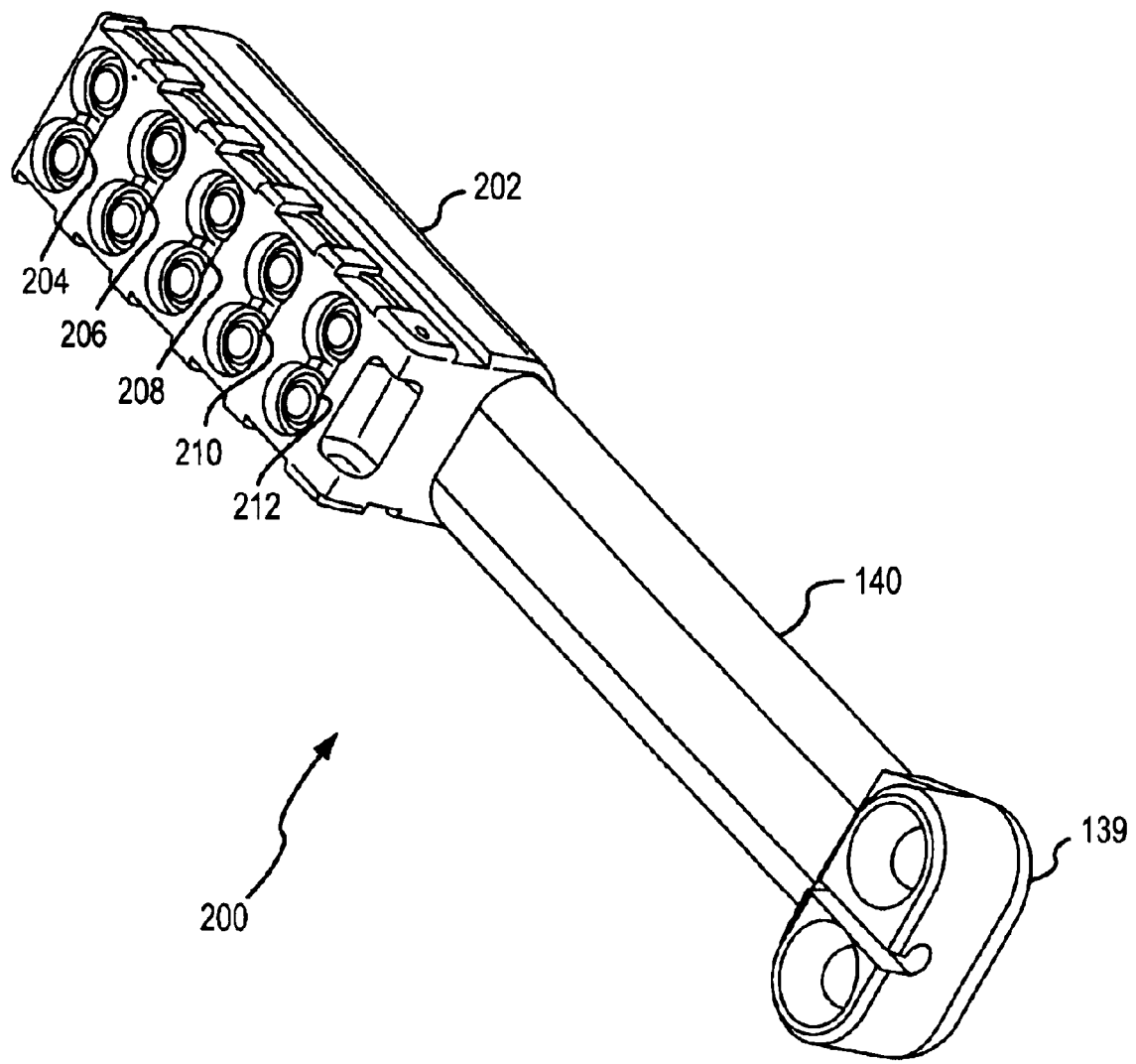
FIG. 10 discloses a geometric view of another configuration of the machine male connector assembly.

Yet another configuration of the male machine connector assembly is disclosed in FIG. 10. In this configuration the connector assembly 200 includes a female connector portion 202 with receiving ends 204-212 for interconnecting with a maximum 5 intermediate male connectors simultaneously. The configurations of the male machine connector assembly, especially the intermediate female connector, are exemplary, and one skilled in the art would know that the female intermediate connector portion can be configured with any number of receiving ends so as to connect with any number of male intermediate connectors. In this configuration it further seen that receiving ends may be incorporated in any number of surfaces of the intermediate female connector so as to facilitate the ergonomic design of the overall system.

The foregoing description of the present invention has been presented for purposed of illustration and description. Furthermore, the description is not intended to limit the invention to the form disclosed herein. Consequently, variations and modifications commensurate with the above teachings, and the skill or knowledge of the relevant art, within the scope of the present invention. The embodiments described hereinabove are further intended to explain best modes known for practicing the invention and to enable others skilled in the art to utilize the invention in such, or other, embodiment and with various modifications required by the particular applications or uses of the present invention. It is intended that the appended claims be construed to include alternative embodiments to the extent permitted by the prior art.

What is claimed is:

1. A system employable for patient temperature control including a medical fluid circulating system including at least one reservoir for circulating a fluid, comprising:
    at least one male connector which is one of: interconnected and interconnectable, to a patient temperature control pad, the male connector including a body portion with a plurality of fluid channels extending therethrough, and an insertion end;
    at least one female connector which is one of interconnected and interconnectable to the medical fluid temperature circulating system which includes a body portion with a plurality of channels extending therethrough, and a receiving end configured to receive and engage the insertion end of the male connector so as to create a plurality of sealed fluid paths through the male and female connectors when engaged;
    said male and female connectors further including at least one orientation device configured such that the male and female connectors are connectable only at a predetermined orientation; and
    an engagement surface included with the female connector and an engagement device included with the male connector, said engagement device being manipulable to engage and disengage the engagement surface when the male and female connectors are engaged.

2. The system of claim 1 wherein the male and female connectors each includes an engagement device and an engagement surface which provides for engagement between said male and female connectors.

3. The system of claim 1 wherein the engagement surface is configured as a ledge incorporated into the body portion of the female connector.

4. The system of claim 3 wherein the engagement device comprises:
    at least one flex arm extending substantially perpendicular from the body portion of the male connector;
    a latch arm positionable at an end of the at least one flex arm away from the body portion of the male connector substantially perpendicular to the latch arm, wherein the latch arm includes a depressible portion configured on a first end and an engagement portion configured on a second end opposite the first end; and
    the flex arm being connectable to the latch arm in a manner such that application of a force to the first end rotates the second end and flex arm about the point of attachment of the flex arm and the body, and removal of the force returns the flex arm and latch arm to the original position.

5. The system of claim 4 wherein the female connector further includes at least one spring loaded valve device locatable within each of the channels of the female connector, wherein the valve device is configured to open and provide the sealed fluid path upon insertion of the insertion end of the male connector in the receiving end of the female connector, and to close and seal the receiving end when the insertion end is removed.

6. The system of claim 5 wherein the engagement surface and engagement device are configured as interlocking lips so as to limit lateral movement of the latch arm when the male and female connectors are engaged and a pressure is exerted between the male and female connectors by the at least one spring loaded valve device in compression.

7. The system of claim 1 wherein the insertion end and the receiving end each include a cross sectional shape through a plane substantially perpendicular to one or more of the centerlines of the fluid channels which is substantially non-symmetrical.

8. The system of claim 1 wherein the orientation device includes at least one of:
    an alignment flange positionable between an opening in the insertion end of the male connector and an orientation member extending between opening in the receiving end of the female connector.

9. The system of claim 1 wherein the female connector is further configured to include a plurality of receiving ends configured to engage a plurality of male connector.

10. The system of claim 1 wherein the engagement device comprises a rotatable engagement device and the engagement surface is configured to receive the rotatable engagement device such that when the rotatable engagement device is received within the engagement surface and is rotated to a first rotational orientation, the male and female connectors are mechanically engaged and when the rotational engagement device is rotated to a second rotation orientation the male and female connectors are disengaged.

11. The system of claim 1 wherein the male connector further includes a one piece hose section having a first end connectable to the body portion opposite the insertion end, wherein the one piece hose section includes a plurality of fluid channels in fluid communication with the fluid channels of the body portion.

12. The system of claim 11 wherein the male connector further includes an intermediate connector device connectable to a second end of the one piece hose section.

13. The system of claim 12 wherein the intermediate connector device comprises a female style connector configured with a one or more receiving ends for interconnecting with a plurality of male style connectors.

14. The system of claim 1 wherein the female connector is mountable on a housing for the medical fluid temperature circulating system.

15. The system of claim 1 wherein the receiving end of the female connector includes at least one O-ring positionable against a tapered surface and the insertion end of the male connector further includes an internal tapered surface within at least one of the channels, wherein upon insertion of the insertion end in the receiving end, the internal tapered surface of the male connector contacts the O-ring and rolls the O-ring along the tapered surface of the female connector so as to compress the at least one O-ring and create a fluid tight seal between the insertion end of the male connector and the receiving end of the female connector.

16. The system of claim 15 wherein the tapered surface of the male connector has a greater taper angle than the tapered surface of the female connector.

17. A method of providing medical fluid circulation for a medical fluid circulating system including at least one reservoir for circulating a fluid, comprising the steps of:
   aligning a first connector, where the first connector is one of: interconnected and interconnectable to a patient temperature control pad, with a second connector, where the second connector is one of interconnected and interconnectable with the medical fluid circulating system, so that fluid channels passing through a body portion of the first connector are aligned with corresponding fluid channels passing through a body portion of the second connector, wherein one of the first and second connectors is a male connector and the other is a female connector;
   interconnecting the first and second connectors in a manner wherein sealed fluid paths are created between each of the fluid channels of the first connector and the corresponding fluid channels of the second connector, wherein interconnecting includes the step of:
      manipulating an engagement device on the male connector to engage an engagement surface on the female connector wherein the step of manipulating comprises a one handed action; and
   circulating the medical fluid through the sealed fluid paths between the medical fluid temperature circulating system and the patient temperature control pad through the first and second connectors in a selected direction.

18. The method of claim 17 wherein the step of aligning comprises identifying at least one orientation device on each of the first and second connectors and positioning the at least one orientation device to avoid interfering contact upon interconnection of the first and second connectors.

19. The method of claim 17 wherein the first connector comprises a male connector and the second connector comprises a female connector.

20. The method of claim 17 wherein the male connector includes a plurality the engagement devices and the female connector includes a plurality engagement surfaces.

21. The method of claim 20 wherein the step of manipulating comprises: simultaneously applying a first force to all the engagement devices at a first location relative to a point of rotation for the engagement device, and rotating the engagement device; and
   upon insertion of the male connector in the female connector to a predetermined point, releasing each of the engagement devices which in turn provides for interlocking of the engagement devices with the engagement surfaces.

22. The method of claim 21 wherein the engagement devices and the engagement surfaces include interlocking lip structures which limit lateral movement of the engagement device when engaged and a compressive force is applied.

23. The method of claim 22 wherein removal of the male connector from the female connector comprises the steps of:
   applying a further insertion force to move the engagement devices clear of the engagement surfaces;
   simultaneously applying the first force to the engagement devices at the first location relative to a point of rotation for the engagement device, and rotating the engagement device away from the body portion of the second connector, and
   reversing the insertion force and moving the male connector clear of the female connector while maintaining simultaneous application of the first force.

24. The method of claim 17 wherein the step of interconnecting comprises:
   positioning at least one internal tapered surface of the fluid channels through the male connector against an O-ring located around an external tapered surface of the fluid channels through the female connector;
   moving the internal tapered surface relative to the external taped surface so as to roll and increasingly apply a compressive force to the O-ring; and
   compressing the O-ring in a manner which creates a fluid tight seal between the male and female connectors so as to create the sealed fluid paths.

25. The method of claim 24 wherein the internal tapered surface has a greater taper angle than the external tapered surface.

26. A patient temperature control assembly comprising:
   a male connector having a body portion with a plurality of fluid channels passing therethrough, and a male connector end;
   a female connector having a body portion with a plurality of fluid channels passing therethrough, and a female receiving end configured to receive and fluidly seal with the male connector end and form a plurality of sealed fluid paths; and
   an engagement device including:
      a rotatable element incorporated into one of the male and female connectors and an engagement surface incorporated into the other of the male and female connectors, the engagement surface being configured to receive the rotatable element, wherein the male and female connector are engaged at a first rotational position for the rotatable element and disengaged at a second rotational position for the rotatable element.
   wherein one of the male and female connectors is attachable to a medical fluid processing system and the other of the male and female connectors is attachable to a patient temperature control pad assembly.

27. The assembly of claim 26 wherein the rotatable element configured to pass within the engagement surface.

28. The assembly of claim 27 wherein the engagement surface comprises a slot configured to allow a portion of the rotatable element to pass at a first rotational orientation and to engage and hold the portion of the rotatable element at a second rotational orientation.

29. The assembly of claim 26 further comprising:
   at least one hose assembly having a first end attachable to one of the male and female connectors and a second end connectable to the patent temperature control pad assembly, wherein the hose assembly includes a plurality of fluid channel.

30. The assembly of claim 29 further including:
an intermediate connector device connectable to the second end of the hose assembly.

31. The assembly of claim 30 wherein the intermediate connector device is configured as a female intermediate connectable to at least one intermediate male connector.

32. The assembly of claim 26 wherein the temperature control pad assembly further includes at least one intermediate connector assembly disposed between one of the male and female connectors and at least one hose portion in connection with the at least one temperature control pad.

33. The assembly of claim 32 wherein the at least one intermediate connector assembly comprises:
a male intermediate connector including a body portion with a plurality of fluid channels passing therethrough and an insertion end;
a female intermediate connector including a body portion with a plurality of fluid channels passing therethrough and at least one receiving end, where the at least one receiving end is configured to receive the insertion end of the male connector and upon insertion of the insertion end in the receiving end creating a scaled fluid path between at least one of the fluid channels and at least one of the fluid paths; and
said male and female intermediate connectors further configured with at least one of external surface feature and an engagement device, so that the male intermediate connector is insertable in the receiving end at only one orientation relative to the female connector.

34. The assembly of claim 33 wherein the female intermediate connector further includes the external surface feature and the male intermediate connector includes the engagement device, the device being manipulable to engage and disengage with an engagement surface of the female connector upon insertion in the receiving end.

35. The assembly of claim 34 wherein the engagement surface is configured as a ledge incorporated into a body portion of the female connector.

36. The assembly of claim 35 wherein the engagement device comprises:
at least one flex arm extending substantially perpendicular from the body portion of the male intermediate connector;
a latch arm positionable at an end of the at least one flex arm away from the body portion substantially perpendicular to the latch arm, wherein the latch arm includes a depressible portion configured on a first end and an engagement portion configured on a second end opposite the first end; and
the flex arm being connectable to the latch arm in a manner such that application of a force to the first end rotates the second end and flex arm about the point of attachment of the flex arm and the body, and removal of the force returns the flex arm and latch arm to the original position.

37. The assembly of claim 36 wherein the female intermediate connector further includes at least one spring loaded valve device locatable within each of the channels, wherein the valve device is configured to open and provide the scaled fluid path upon insertion of the insertion end in the receiving end, and to close and seal the receiving end when the male intermediate connector is removed.

38. The assembly of claim 36 wherein the engagement surface and engagement device are configured as interlocking lips so as to limit lateral movement of the latch arm when the male and female intermediate connectors are engaged and a pressure is exerted between the male and female intermediate connectors by the at least one spring loaded valve device in compression.

39. The assembly of claim 33 wherein the body portion of at least one of the male and female intermediate connectors includes a cross sectional shape through a plane substantially perpendicular to one or more of the centerlines of the fluid channels which is substantially non-symmetric.

40. The assembly of claim 33 wherein the body portion of the male and female intermediate connectors further includes at least one of: an alignment flange positionable between the channels and an orientation member positionable between the channels which provide for the engagement of the male and female intermediate connectors at the predetermined orientation.

41. The assembly of claim 33 wherein the female intermediate connector is further configured to include a plurality of receiving ends so as to receive and interconnect with a plurality of the male intermediate connectors.

42. The assembly of claim 33 wherein the receiving end of the female intermediate connector includes at least one O-ring positionable against a tapered surface and the insertion end of the male connector further includes an internal tapered surface within at least one of the channels, wherein upon insertion of the insertion end in the receiving end, the internal tapered surface of the male intermediate connector contacts the O-ring and rolls the O-ring along the tapered surface of the female intermediate connector so as to compress the at least one O-ring and create a fluid tight seal between the insertion end of the male intermediate connector and the receiving end of the female intermediate connector.

43. The assembly of claim 42 wherein the tampered surface of the male intermediate connector has a greater taper angle than the tapered surface of the female intermediate connector.

44. A patient temperature control pad assembly, comprising:
a male machine connector including a body portion with a plurality of fluid channel formed therethrough, the male machine connector further including an insertion end which is insertable in a receiving end of a female machine connector so as to fluidly seal with the female connector end and establish a plurality of sealed fluid paths through the male and female machine connectors;
said male machine connector further including at least one engagement portion integrated in the male machine connector configured to receive a rotatable engagement device, the at least one engagement portion being further configured such that when the rotation device is within the engagement portion and is rotated to a predetermined orientation, the male and female machine connectors are mechanically engaged; and
at least one hose assembly attachable to the male machine connector portion and in communication with the fluid channels of the male connector, where said at least one hose assembly is configured to provide for multidirectional circulation of the medical fluid therethrough; and
at least one patient temperature control pad connectable to the hose assembly and configured to receive, circulate, and return the medical fluid to the hose assembly.

45. The assembly of claim 44 wherein the engagement portion is a slot configured to allow a portion of the rotatable engagement device to pass within at a first rotational orientation and to mechanically engage the rotatable engagement device at a second rotational orientation.

46. The assembly of claim 44 wherein the male machine connector further includes a one piece hose section connectable to the body portion opposite the insertion end, wherein the one piece hose section includes a plurality of fluid channels in fluid communication with the fluid channels of the body portion.

47. The assembly of claim 46 wherein the male machine connector further includes an intermediate connector device connectable to the one piece hose section at an end opposite the body portion.

48. The assembly of claim 44 wherein the temperature control pad assembly further includes at least one intermediate connector assembly, wherein the intermediate connector assembly is configured to provided a sealed connection between an intermediate male connector and at least one hose portion interconnectable with the at least one temperature control.

49. The assembly of claim 44 wherein the temperature control pad assembly further includes at least one intermediate connector assembly, wherein the intermediate connector assembly is configured to provide a sealed connection between the male machine connector and at least one hose portion in connection with the at least one temperature control pad.

50. The assembly of claim 49 wherein the at least one intermediate connector assembly comprises:
a male intermediate connector including a body portion with a plurality of fluid channels extending from a first end to a second end, wherein each of the fluid channels exits the body portion through one of a plurality of connection ends formed in the body portion;
a female intermediate connector attachable to a second hose apparatus and configured with a plurality of fluid channels passing therethrough and at least one receiving end, where the at least one receiving end is configured to receive the first end of the male connector and upon insertion of the male connector first end in the receiving end creating a sealed fluid path between at least one of the fluid channels and at least one of the fluid paths; and
said male and female intermediate connectors further configured with at least one external surface feature so that the male intermediate connector is insertable in the receiving end at only one orientation relative to the female intermediate connector.

51. The assembly of claim 50 wherein the male and female intermediate connectors each include at least one of: an external connection device and engagement surface which provides for engagement between said intermediate connectors.

52. The assembly of claim 51 wherein the female intermediate connector further includes the engagement surface and the male intermediate connector includes the engagement device which is manipulable to engage and disengage with the engagement surface of the female intermediate connector upon insertion in the receiving end.

53. The assembly of claim 52 wherein the engagement surface is configured as a ledge incorporated into a body portion of the female intermediate connector.

54. The assembly of claim 53 wherein the engagement device comprises:
at least one flex arm extending substantially perpendicular from the body portion of the male intermediate connector;
a latch arm positionable at an end of the at least one flex arm away from the body substantially perpendicular to the latch arm, wherein the latch arm includes a depressible portion configured on a first end and an engagement portion configured on a second end opposite the first end; and
the flex arm being connectable to the latch arm in a manner such that application of a force to the first end rotates the second end and flex arm about the point of attachment of the flex arm and the body, and removal of the force returns the flex arm and latch arm to the original position.

55. The assembly of claim 54 wherein the female intermediate connector further includes at least one spring loaded valve device locatable within each of the channels, wherein the valve device is configured to open and provide the sealed fluid path upon insertion of the male connection end in the receiving end, and to close and seal the receiving end when the male intermediate connector is removed.

56. The assembly of claim 55 wherein the engagement surface and engagement device are configured as interlocking lips so as to limit lateral movement of the latch arm when the male and female intermediate connectors are engaged and a pressure is exerted between the male and female intermediate connectors by the at least one spring loaded valve device in compression.

57. The assembly of claim 49 wherein the body portion of the male machine connector is configured to include a cross sectional shape through a plane substantially perpendicular to one or more of the centerlines of the fluid channels which is substantially non-symmetrical.

58. The assembly of claim 49 wherein the body portion of the male and female machine connector further includes at least one of: an alignment flange positionable between the fluid channels and an orientation member positionable between the channels which provide for the engagement of the male and female machine connectors at the predetermined orientation.

59. The assembly of claim 49 wherein the female machine connector is further configured to include a plurality of the receiving ends so as to receive and interconnect with a plurality of the male machine connectors.

60. The assembly of claim 49 wherein receiving end of the female machine connector includes at least one O-ring positionable against a tapered surface and the insertion end of the male machine connector further includes an internal tapered surface within at least one of the channels, wherein upon insertion of the insertion end in the receiving end, the internal tapered surface of the male machine connector contacts the O-ring and rolls the O-ring along the tapered surface of the female machine connector so as to compress the at least one O-ring and create a fluid tight seal between the insertion end of the male connector and the receiving end of the female machine connector.

61. The assembly of claim 60 wherein the tapered surface of the male machine connector has a greater taper angle than the tapered surface of the female machine connector.

62. A system employable for patent temperature control including a medical fluid circulating system including at least one reservoir for circulating a fluid, comprising:
at least one male connector which is one of: interconnected and interconnectable, to a patient temperature control pad, the male connector including a body portion with a plurality of fluid channels extending therethrough, and an insertion end;
at least one female connector apparatus which is one of interconnected and interconnectable to the medical fluid temperature circulating system which includes a body portion with a plurality of channels extending therethrough, and a plurality of receiving ends configured to receive and engage the insertion end of at least two male connectors so as to create a plurality of sealed fluid paths with the male connectors when engaged;

wherein at least one of the male and female connectors further includes at least one orientation device configured such that the male and female connectors are connectable only at a predetermined orientation.

63. The system of claim 62, wherein the female connector further includes an engagement surface; and each male connector further includes an engagement device manipulable to engage and disengage with the engagement surface of the female connector when the male and female connectors are engaged.

64. The system of claim 63, wherein the engagement surface is configured as a ledge incorporated into the body portion of the female connector.

65. The system of claim 64 wherein the engagement device comprises:

at least one flex arm extending substantially perpendicular from the body portion of the male connector;

a latch arm positionable at an end of the at least one flex arm away from the body portion of the male connector substantially perpendicular to the latch arm, wherein the latch arm includes a depressible portion configured on a first end and an engagement portion configured on a second end opposite the first end; and the flex arm being connectable to the latch arm in a manner such that application of a force to the first end rotates the second end and flex arm about the point of attachment of the flex arm and the body, and removal of the force returns the flex arm and latch arm to the original position.

66. The system of claim 62 wherein one of the female connector and the male connectors includes a rotatable engagement device and the other of the female connector and the male connectors includes an engagement portion configured to receive the rotatable engagement device, the engagement portion being further configured such that when the rotatable engagement device is within the engagement portion and is rotated to a first rotational orientation, the male and female connectors are mechanically engaged and when the rotational engagement device is moved to a second rotation orientation the male and female connectors are disengaged.

67. A patient temperature control assembly comprising:

a male connector having a body portion with a plurality of fluid channels passing therethrough, and a male insertion end;

a female connector having a body portion with a plurality of fluid channels passing therethrough, and a female receiving end configured to receive and fluidly seal with the male insertion end and form a plurality of sealed fluid paths, wherein one of the male and female connectors is attachable to a medical fluid processing system and the other of the male and female connectors is attachable to a patient temperature control pad assembly;

an engagement device included with one of the male and female connectors and an engagement slot included within the other of the male and female connectors, wherein the engagement device is selectively moveable from a first orientation to a second orientation and wherein the engagement device is operative to pass through the engagement slot in the first orientation surface and is restrainably engaged in the slot in the second orientation.

68. The assembly of claim 67 wherein the engagement member is configured to pass through the slot in the first orientation and is configured to be restrained in the slot in the second orientation.

69. The assembly of claim 67 wherein the slot has a first portion with a first cross-width and a second portion with a second cross-width, wherein the second cross-width is greater than the first cross-width.

70. The assembly of claim 69 wherein the first portion extends through a surface of the body portion of the one of the male and female connectors and the second portion is formed substantially within the body portion of the one of the male and female connectors.

71. The assembly of claim 69 wherein in the engagement device has first and second profiles in the first and second orientations, respectively, wherein one of the profiles has a cross-width less than the cross-width of the first portion of the engagement slot and the other profile has a cross-width greater than the cross-width of the first portion of the engagement slot.

72. The assembly of claim 67 wherein the engagement device comprises a shaft for interfacing with the slot and a lever interconnected to the shaft for rotating the shaft from the first orientation to the second orientation.

73. The assembly of claim 72 wherein said shaft rotates about a longitudinal center axis.

74. The assembly of claim 67 wherein the engagement device is configured such that the male and female connectors are connectable only at a predetermined orientation.

75. The assembly of claim 67 wherein the female connector is further configured to include a plurality of receiving ends configured to engage a plurality of male connectors.

76. The assembly of claim 67 wherein the female connector further includes at least one spring loaded valve device locatable within each of the channels, wherein the valve device is configured to open and provide the sealed fluid path upon insertion of the male insertion end in the female receiving end, and to close and seal the receiving end when the male connector is removed.

77. A patient temperature control assembly comprising:

a male connector having:
    a body portion with a plurality of fluid channels passing therethrough; and
    a male insertion end;

a female connector having:
    a body portion with a plurality of fluid channels passing therethrough; and
    a female receiving end configured to receive and fluidly seal with the male insertion end and form a plurality of sealed fluid paths, wherein one of the male and female connectors is attachable to a medical fluid processing system and the other of the male and female connectors is attachable to a patient temperature control pad assembly;

an engagement device included with one of the male and female connectors and an engagement surface included with the other of the male and female connectors, wherein, a first portion of the engagement device is configured to move one of laterally inward and laterally outward from a first orientation to a second orientation in response to a laterally inward force being applied to a second portion of the engagement device and wherein, the engagement device restrainably engages the engagement surface in one of the first and second orientations and disengaged the engagement surface in the other the of the first and second orientations.

78. The assembly of claim 77 wherein the engagement device comprises an arm interconnected to a body portion of one of the male and female connectors, wherein the arm is operative to flex between the first orientation and the second orientation.

79. The assembly of claim 78 wherein said engagement device comprises first and second arms interconnected to a body portion of one of the male and female connectors, wherein each arm is operative to flax between first orientation and the second orientations.

80. The assembly of claim 79 wherein said first and second arms are disposed on opposing surface of the body portion such that the first and second arms engage opposing surfaces on the other of the male and female connectors.

81. The assembly of claim 78 wherein the engagement surface is configured as a ledge incorporated into a body portion of the other of the male and female connectors.

82. The assembly of claim 81 wherein the engagement surface and a portion of the arm are configured as interlocking lips.

83. The assembly of claim 78 wherein the arm further comprises:

at least one flex arm extending substantially perpendicular from a body portion of the one of the male and female connectors;

a latch arm positionable at an end of the at least one flex arm away from the body portion of the one of the male and female connectors substantially perpendicular to the latch arm, wherein the latch arm includes a depressible portion configured on a first end and an engagement portion configured on a second end opposite the first end; and the flex arm being connectable to the latch arm in a manner such that application of a lateral inward force to the first end rotates the second end and flex arm about the point of attachment of the flex arm and the body, and removal of the force returns the flex arm and latch arm to the original position.

84. The assembly of claim 77 wherein one of the male and female connectors further includes:

at least one orientation device configured such that the male and female connectors are connectable only at a predetermined orientation.

85. The assembly of claim 77 wherein the female connector is further configured to include a plurality of female receiving ends configured to engage a plurality of male connectors.

86. The assembly of claim 77 wherein the female connector further includes at least one spring loaded valve device locatable within each of the channels, wherein the valve device is configured to open and provide the sealed fluid path upon insertion of the male insertion end in the female receiving end, and to close and seal the receiving end when the male connector is removed.

* * * * *

UNITED STATES PATENT AND TRADEMARK OFFICE
CERTIFICATE OF CORRECTION

PATENT NO.    : 6,827,728 B2
DATED         : December 7, 2004
INVENTOR(S)   : Ellingboe et al.

It is certified that error appears in the above-identified patent and that said Letters Patent is hereby corrected as shown below:

Column 9,
Line 22, delete "to.move", and insert therefor -- to move --.

Column 13,
Line 49, after "of", insert -- : --.

Column 14,
Line 49, delete "connector", and insert therefor -- connectors --.

Column 17,
Line 3, delete "channel", and insert therefor -- channels --;
Lines 25 and 62, delete "scaled", and insert therefor -- sealed --.

Column 18,
Line 34, delete "tampered", and insert therefor -- tapered --;
Line 41, delete "channel", and insert therefor -- channels --.

Column 19,
Line 17, after "control", insert -- pad --;
Line 21, delete "scaled", and insert -- sealed --.

Column 20,
Line 31, delete "connector", and insert therefor -- connectors --;
Line 64, after "of", insert -- : --.

UNITED STATES PATENT AND TRADEMARK OFFICE
CERTIFICATE OF CORRECTION

PATENT NO. : 6,827,728 B2
DATED : December 7, 2004
INVENTOR(S) : Ellingboe et al.

It is certified that error appears in the above-identified patent and that said Letters Patent is hereby corrected as shown below:

Column 23,
Line 7, delete "flax", and insert therefor -- flex --;
Line 10, delete "surface", and insert therefor -- surfaces --.

Signed and Sealed this

Twenty-fifth Day of October, 2005

JON W. DUDAS
*Director of the United States Patent and Trademark Office*